(12) United States Patent
Medhekar et al.

(10) Patent No.: US 8,969,606 B2
(45) Date of Patent: Mar. 3, 2015

(54) CALCINATION AND REDUCTION PROCESS INCLUDING A FLUIDIZING BED REACTOR

(75) Inventors: Vinay Medhekar, Beaumont, TX (US); John J. Ostermaier, Orange, TX (US); Michael C. Quinn, III, Kingwood, TX (US); Colin S. Slaten, Orange, TX (US)

(73) Assignee: INVISTA North America S.a r.l., Wilmington, DE (US)

( * ) Notice: Subject to any disclaimer, the term of this patent is extended or adjusted under 35 U.S.C. 154(b) by 197 days.

(21) Appl. No.: 13/490,116

(22) Filed: Jun. 6, 2012

(65) Prior Publication Data

US 2013/0144079 A1 Jun. 6, 2013

Related U.S. Application Data

(60) Provisional application No. 61/495,784, filed on Jun. 10, 2011, provisional application No. 61/495,789, filed on Jun. 10, 2011.

(51) Int. Cl.
| | |
|---|---|
| *C22B 23/00* | (2006.01) |
| *C07F 15/04* | (2006.01) |
| *C22B 23/02* | (2006.01) |
| *B01J 31/18* | (2006.01) |
| *B01J 31/22* | (2006.01) |
| *C07F 19/00* | (2006.01) |

(52) U.S. Cl.
CPC ............ *C22B 23/02* (2013.01); *B01J 31/1845* (2013.01); *B01J 31/185* (2013.01); *C22B 23/021* (2013.01); *B01J 31/22* (2013.01); *C07F 19/005* (2013.01); *B01J 2231/322* (2013.01); *B01J 2531/847* (2013.01)
USPC ................... 556/13; 75/629; 75/711; 75/717; 423/141

(58) Field of Classification Search
USPC ................ 556/13; 75/629, 711, 717; 423/141
See application file for complete search history.

(56) References Cited

U.S. PATENT DOCUMENTS

| | | | |
|---|---|---|---|
| 2,913,348 A | 11/1959 | Jackson et al. | |
| 3,350,167 A | 10/1967 | Mcmullen et al. | |
| 3,399,050 A | 8/1968 | Evans et al. | |
| 3,496,215 A | 2/1970 | Drinkard et al. | |
| 3,496,217 A | 2/1970 | Drinkard et al. | |
| 3,631,191 A | 12/1971 | Kane et al. | |
| 3,655,723 A | 4/1972 | Drinkard et al. | |
| 3,672,873 A | 6/1972 | Huggins et al. | |
| 3,766,237 A | 10/1973 | Chia et al. | |
| 3,816,098 A | 6/1974 | Mackiw et al. | |
| 3,846,461 A | 11/1974 | Shook, Jr. | |
| 3,847,959 A | 11/1974 | Shook, Jr. et al. | |
| 3,903,120 A | 9/1975 | Shook, Jr. et al. | |
| 3,914,124 A * | 10/1975 | O'Neill et al. .................. | 75/430 |
| 4,118,342 A | 10/1978 | Debus et al. | |
| 4,416,825 A | 11/1983 | Ostermaier | |
| 4,591,579 A | 5/1986 | Lok et al. | |
| 4,670,416 A | 6/1987 | Klimmek et al. | |
| 4,749,801 A | 6/1988 | Beatty et al. | |
| 4,946,068 A | 8/1990 | Erickson et al. | |
| 5,087,599 A | 2/1992 | Botman et al. | |
| 5,512,696 A | 4/1996 | Kreutzer et al. | |
| 5,688,986 A | 11/1997 | Tam et al. | |
| 5,723,641 A | 3/1998 | Tam et al. | |
| 5,981,722 A | 11/1999 | Chen et al. | |
| 6,069,267 A | 5/2000 | Tam et al. | |
| 6,171,996 B1 * | 1/2001 | Garner et al. .................. | 502/162 |
| 6,494,931 B1 | 12/2002 | Mukuno et al. | |
| 6,524,994 B1 | 2/2003 | Reesink et al. | |
| 7,056,565 B1 | 6/2006 | Cai et al. | |
| 7,345,006 B2 | 3/2008 | Bartsch et al. | |
| 7,470,805 B2 | 12/2008 | Rosier et al. | |
| 7,528,275 B2 | 5/2009 | Bartsch et al. | |
| 7,531,682 B2 | 5/2009 | Galland et al. | |
| 7,629,484 B2 | 12/2009 | Ritter et al. | |
| 7,854,973 B2 | 12/2010 | Dey | |
| 2003/0100802 A1 | 5/2003 | Shapiro | |
| 2004/0106815 A1 | 6/2004 | Ritter | |
| 2008/0015381 A1 | 1/2008 | Foo et al. | |
| 2011/0196168 A1 | 8/2011 | Ostermaier | |
| 2013/0143730 A1 | 6/2013 | Fraga-Dubreuil et al. | |
| 2013/0144082 A1 | 6/2013 | Fraga-Dubreuil et al. | |
| 2013/0345459 A1 | 12/2013 | Ostermaier | |

FOREIGN PATENT DOCUMENTS

| | | |
|---|---|---|
| CH | 127157 A | 8/1928 |
| CN | 1765549 A | 5/2006 |
| CN | 101016173 A | 8/2007 |
| CN | 101519229 A | 9/2009 |
| CN | 101708868 A | 5/2010 |

(Continued)

OTHER PUBLICATIONS

International Application Serial No. PCT/US2012/041107, International Preliminary Report on Patentability dated Oct. 17, 2013, 28 pgs.
International Application Serial No. PCT/US2012/041107, International Search Report mailed Mar. 15, 2013, 5 pgs.
International Application Serial No. PCT/US2012/041107, Response filed Jun. 17, 2013 to Written Opinion mailed Mar. 15, 2013, 9 pgs.
International Application Serial No. PCT/US2012/041107, Written Opinion mailed Mar. 15, 2013, 14 pgs.
"Nickel, Palladium and Platinum", In: *Chemistry of the Elements (1st Edition)*, Greenwood, N. N., et al., Pergamon Press, Oxford, (1984), p. 1355.
Formanek, Lothar, et al., "Iron, 3. Direct Reduction Processes", In: *Ullmann's Encyclopedia of Industrial Chemistry*, vol. 19, Wiley-VCH Verlag GmbH & Co., Weinheim, Germany, (2000), 711-726.

(Continued)

*Primary Examiner* — Porfirio Nazario Gonzalez
(74) *Attorney, Agent, or Firm* — Robert B. Furr, Jr.; Nicholas P. Lanzatella

(57) ABSTRACT

These disclosures relate to preparing nickel metal (Ni(0)) suited for use in catalyst systems, such as nickel complexes with phosphorus-containing ligands, useful to catalyze the hydrocyanation of ethylenically unsaturated compounds. The methods described herein can include use of steam during reduction of nickel.

35 Claims, 6 Drawing Sheets

(56) References Cited

FOREIGN PATENT DOCUMENTS

| | | |
|---|---|---|
| CN | 101733106 A | 6/2010 |
| EP | 114704 A2 | 8/1984 |
| EP | 0354612 B1 | 12/1991 |
| EP | 496448 B1 | 3/1994 |
| EP | 673841 A2 | 9/1995 |
| EP | 0985448 A1 | 3/2000 |
| FI | 115522 B | 5/2005 |
| FR | 1400059 A | 5/1965 |
| GB | 146407 A | 11/1921 |
| GB | 255884 A | 4/1927 |
| GB | 703826 A | 2/1954 |
| GB | 1437191 A | 5/1976 |
| GB | 1437192 A | 5/1976 |
| JP | 5896802 A | 6/1983 |
| JP | 61106422 A | 5/1986 |
| JP | 1153534 A | 6/1989 |
| JP | 2172829 A | 7/1990 |
| JP | 2001335326 A | 12/2001 |
| RU | 2102137 C1 | 1/1998 |
| SU | 116020 A1 | 11/1958 |
| SU | 254781 A | 10/1969 |
| SU | 710958 A1 | 1/1980 |
| WO | 2006052677 A1 | 5/2006 |
| WO | 2010088863 A1 | 8/2010 |
| WO | WO-2011/075494 A1 | 6/2011 |
| WO | WO-2011/075496 A1 | 6/2011 |
| WO | 2011094411 A1 | 8/2011 |
| WO | WO-2012/170297 A2 | 12/2012 |
| WO | WO-2012/170300 A2 | 12/2012 |
| WO | WO-2012/170537 A2 | 12/2012 |

OTHER PUBLICATIONS

Kerfott, Derek G.E., "Nickel", In: *Ullmann's Encyclopedia of Industrial Chemistry*, vol. 24, Wiley-VCH Verlag GmbH & Co., Weinheim, DE, (2000), 37-101.

Lascelles, K., "Nickel Compounds", In: *Ullman's Encyclopedia of Industrial Chemistry*, vol. 24, Wiley VCH Verlag GmbH & Co., Weinheim, Germany, (2005), 117-131.

Richardson, Y., et al., "In situ generation of Ni metal nanoparticles as catalyst for $H_2$-rich syngas production from biomass gasification", *Applied Catalysis A: General*, 382(2), (2010), 220-230.

Taylor, N.J., et al., "Synthesis and Crystal Structure of the Novel Cyclometallophosphine Complex $Re_4Cl_2(CO)_{15}$-{MePP(Me)PMe}", *Journal of the Chemical Society, Chemical Communications*, 8, (1985), 476-477.

Brunauer et al., "Adsorption of Gases in Multimolecular Layers", J. Am. Chem. Soc. 60, 1938, pp. 309-319.

Carlsson et al., "Coprecipitation of Ni with CaCO3: an Experimental Study", Report, VIT-TIED-1712, VTT/RN-1712, ISBN-951-38-4866-3; Order No. PB96-187497GAR, Avail.: NTIS From: Gov. Rep. Announce. Index (U. S.), 96 (17), Abstract No. 17-01,973, Chemical Technol., Valtion Teknillinen Tutkimuskeskus, Espoo, Finland, Copyright: 2010 ACS on STN, 1996, 29 pages.

Carriel et al., "Composition of Basic Nickel Carbonates", Journal of the American Chemical Society, 76, CODEN: JACSAT; ISSN: 0002-7863, Mellon Inst., Pittsburgh, PA, Copyright: 2010 ACS on STN, 1954, pp. 3839-3843.

Chen et al., "Resistivity to Sulfur Poisoning of Nickel-Alumina Catalysts", Ind. Eng. Chem. Res. 27(8), 1988, pp. 1391-1396.

Costodes, Taty V.C, "Reactive Crystallization of Nickel Hydroxy-Carbonate in Fluidized-Bed Reactor: Fines Production and Column Design", Chemical Engineering Science, 61(5), CODEN: CESCAC; ISSN: 0009-2509, Precipitation and Crystallization Research Facility, Department of Chemical Engineering, University of Cape Town, Cape Town, S. Afr., Copyright: 2010 ACS on STN, 2006, pp. 1377-1385.

Crosa et al., "Determination of Mean Crystalite Dimensions from X-Ray Diffraction Peak Profiles: A Comparative Analysis of Synthetic Hematites", Clays and Clay Materials, 47(6), 1999, pp. 742-747.

Davidson et al., "Nucleation Kinetics in the Reactions of Nickel Basic Carbonates with Hydrogen Sulfide: The Carbonate Precipitation Reactions of Divalent Nickel", Industrial & Engineering Chemistry Research, 46(14), CODEN: IECRED; ISSN: 0888-5885, School of Engineering and Electronics, University of Edinburgh, Edinburgh, EH9 3JL, UK, Copyright: 2010 ACS on STN, 2007, pp. 4772-4777.

Evlash et al., "Precipitation of Basic Nickel Carbonate", Zhurnal Prikladnoi Khimii (Sankt-Peterburg, Russian Federation), 58(11), CODEN: ZPKHAB; ISSN: 0044-4618, Copyright: 2010 ACS on STN, 1985, pp. 2417-2421.

Gagnon et al., "Study of the Precipitation of Carbonates, Borates, Silicates and Arsenates", Canadian Journal of Research, Section B: Chemical Sciences, 19, B, CODEN: CNRBAX; ISSN: 0366-7391, Copyright: 2010 ACS on STN, 1941, pp. 179-204.

Guillard et al., "Nickel Carbonate Precipitation in a Fluidized-ed Reactor", Industrial & Engineering Chemistry Research, 40(23), CODEN: IECRED; ISSN: 0888-5885, Precipitation and Crystallization Research Facility Chemical Engineering Department, University of Cape Town, Rondebosch, 7701, S. Afr., Copyright: 2010 ACS on STN, 2001, pp. 5564-5569.

Guillard et al., "Optimization of Nickel Hydroxycarbonate Precipitation Using a Laboratory Pellet Reactor", Industrial & Engineering Chemistry Research, 41(13), CODEN: IECRED; ISSN: 0888-5885, Precipitation and Crystallisation Research Facility, Chemical Engineering Department, University of Cape Town, Cape Town, 7701, S. Afr., Copyright: 2010 ACS on STN, 2002, pp. 3110-3114.

Hoffmann et al., "Preliminary Results on the Behavior of Ni(li) in the Calcite-Water System", Mineralogical Magazine, 62A(Pt. 2), CODEN: MNLMBB; ISSN: 0026-461X, Geological Institute, University of Copenhagen, Copenhagen, DK-1350, Den., Copyright: 2010 ACS on STN, 1998, pp. 642-643.

Jaulmes et al., "Solubility and Precipitation of Slightly Soluble Salts of Weak or Moderately Strong Acids", Travaux de la Societe de Pharmacie de Montpellier, 25(2), CODEN: TSPMA6; ISSN: 0037-9115, University Montpellier, Fr., Copyright: 2010 ACS on STN, 1965, pp. 98-110.

Lewis, A. E., "Fines Formation (and prevention) in Seeded Precipitation Processes", KONA, 24, CODEN: KONAE7; ISSN: 0288-4534, Crystallization and Precipitation Unit, Department of Chemical Engineering, University of Cape Town, Cape Town, 7701, S. Afr., Copyright: 2010 ACS on STN, 2006, pp. 119-125.

Li et al., "Formation of Dispersive NiO Nano-particles via Hydrothermal Modification", Xiyou Jinshu Cailiao yu Gongcheng (Rare Metal Materials and Engineering), 33, (4), Graphs, Spectra, Photomicrographs, 13 reference, Published by: Northwest Institute for Non-Ferrous Metal Research, Editorial Office of Rare Metal Materials and Engineering, Xi'an Shaanxi, 710016, China ISSN: 1002-185X, Tsinghua University (China), Copyright: 2010 CSA on STN, Apr. 2004, pp. 425-428.

Mallya et al., "Basic Nickel Carbonates. I. Factors which Influence the Precipitation of Nickel Carbonates", Journal of the Indian Institute of Science, 43, CODEN: JIISAD; ISSN: 0019-4964, Indian Inst. Sci., Bangalore, Copyright: 2010 ACS on STN, 1961, pp. 44-51.

Mallya et al., "Basic Nickel Carbonates. II. Hydration of Basic Nickel Carbonate", Journal of the Indian Institute of Science, 43, CODEN: JIISAD; ISSN: 0019-4964, Indian Inst. Sci., Bangalore, Copyright: 2010 ACS on STN, 1961, pp. 65-75.

Mallya et al., "Basic Nickel Carbonates. III. Potentiometric Investigation of the Precipitation", Journal of the Indian Institute of Science, 43, CODEN: JIISAD; ISSN: 0019-4964, Indian Inst. Sci., Bangalore, Copyright: 2010 ACS on STN, 1961, pp. 76-86.

Mallya et al., "Basic Nickel Carbonates. IV. Preparation of Basic Nickel Carbonate and Its Differential Thermal Analysis", Journal of the Indian Institute of Science, 43, From: CZ 1962(34), 12221-2. CODEN: JIISAD; ISSN: 0019-4964, Indian Inst. Sci., Bangalore, Copyright: 2010 ACS on STN, 1961, pp. 87-96.

Mallya et al., "Basic Nickel Carbonates. V. Thermogravimetric Behavior of Basic Nickel Carbonates", Journal of the Indian Institute of Science, 43(3), CODEN: JIISAD; ISSN: 0019-4964, Indian Inst. Sci., Bangalore, Copyright: 2010 ACS on STN, 1961, pp. 131-140.

(56) References Cited

OTHER PUBLICATIONS

Mallya et al., "Basic Nickel Carbonates. VI. Thermal Decomposition of Basic Nickel Carbonates in Vacuum and the Nature of the Surfaces", Journal of the Indian Institute of Science, 43(3), CODEN: JIISAD; ISSN: 0019-4964, Indian Inst. Sci., Bangalore, Copyright: 2010 ACS on STN, 1961, pp. 141-147.

Mallya et al., "Basic Nickel Carbonates. VII. Formation and Configurations of Basic Nickel Carbonates", Journal of the Indian Institute of Science, 43(3), From: CZ 1964(49), Abstract No. 0597-9. CODEN: JIISAD; ISSN: 0019-4964, Indian Inst. Sci., Bangalore, Copyright: 2010 ACS on STN, 1961, pp. 148-157.

Lee et al., "A Study on Nickel Hydroxide Crystallization Characteristics", Korean Journal of Chemical Engineering 22(5), CODEN: KJCHE6, ISSN: 0256-1115, Dept. Of Chemical Engineering, Kongju National University, Kongju, 314-701, S. Korea, Copyright: 2010 ACS on STN, 2005, pp. 712-716.

Minkova et al., "Precipitation Processes in Obtaining Basic Nickel(II) Carbonate and Coprecipitation of Other Basic Nickel Salts. I. Preparation of Basic Nickel Carbonate Free of Sulfate Ions", Izvestiya po Khimiya, 13(2), CODEN: IZKHDX; ISSN: 0324-0401, Chemical Reagents Prepare Laboratory, Sofia, 1040, Bulg., Copyright: 2010 ACS on STN, 1980, pp. 222-228.

Minkova et al., "Precipitation Processes in Obtaining Nickel(II) Hydroxocarbonate and Co-Precipitation of Other Nickel Hydroxo Salts. II. Influence of the Conditions for Obtaining Nickel(II) Hydroxocarbonate on the Amount of Co-Precipitated Sulfate Ions", Izvestiya po Khimiya, 16(4), 432-5 CODEN: IZKHDX; ISSN: 0324-0401, Inorg. Salts Res. Laboratory, Sofia, 1040, Bulg., Copyright: 2010 ACS on STN, 1983, pp. 432-435.

Nassler, J., "A New Type of Basic Nickel(II) Carbonate", Collection of Czechoslovak Chemical Communications 29(1), CODEN: CCCCAK; ISSN: 0010-0765, Karlova University, Prague, Copyright: 2010 ACS on STN, 1964, pp. 168-173.

Ozheredova et al., "Nickel-Containing Rinsing Waters. Effect of Additives and the Nature of the Precipitant on the Degree of Treatment", Khimichna Promislovist Ukraini (Kiev, Ukraine), (3), CODEN: KPUKB8, Vostochnoukr. Nats. University im. V. Dalya, Ukraine, Copyright: 2010 ACS on STN, 2005, pp. 41-43.

Packter et al., "Precipitation of Basic Nickel Carbonate Powders from Aqueous Solution. Crystallite Numbers, Composition, and Final Sizes", Kristall und Technik 10(9), CODEN: KRTEAW; ISSN: 0023-4753, Chemical Dep., North-East London Polytech., London UK, Copyright: 2010 ACS on STN, pp. 985-994.

Pistorius, C.W.F.T, "High-Pressure Preparation and Structure of Crystalline Nickelous Carbonate", Experientia 15, CODEN: EXPEAM; ISSN: 0014-4754, University of California, Los Angeles, Copyright: 2010 ACS on STN, 1959, pp. 328-329.

Rhamdhani, et al., "Metallurgical and Materials Transactions B2008", vol. 398, pp. 218-233 and 234-245.

Rossetti-Francois et al., "Structure and Constitution of Basic Nickel Carbonates", Journal de Chimie Physique et de Physico-Chimie Biologique, 51, CODEN: JCPBAN; ISSN: 0021-7689, Sorbonne, Paris, Copyright: 2010 ACS on STN, 1954, pp. 451-460.

Sergeev, M., "Influence of the Temperature on Precipitation of Nickel Carbonate", Masloboino-Zhirovoe Delo, (No. 11), 15 CODEN: MZHDAD; ISSN: 0369-304X,2010 ACS on STN, 1928.

Tolman et al., "Homogeneous Nickel-Catalyzed Olefin Hydrocyanation", Advances in Catalysis, 33, 1985, pp. 1-46.

Ueno et al., "Influence of the Conditions of Precipitation on the Activity of Nickel Catalysts. II. Precipitation with Sodium Carbonate", Kogyo Kagaku Zasshi, 46, CODEN: KGKZA7; ISSN: 0368-5462, Copyright: 2010 ACS on STN, 1943, pp. 45-47.

Vasserman et al., "Continuous Method for the Precipitation of Basic Nickel Carbonate by an Automated Process", Tsvetnye Metally (Moscow, Russian Federation), 37(12), CODEN: TVMTAX; ISSN: 0372-2929, Copyright: 2010 ACS on STN, 1964, pp. 25-31.

Vasserman et al., "Separation of Substances from Solutions by Chemical Precipitation. I. Chemical Aging of Basic Nickel Carbonate Precipitates and the Mechanism of Sodium Carbonate Utilization in the Process of Precipitation", Zhurnal Prikladnoi Khimii (Sankt-Peterburg, Russian Federation), 31, CODEN: ZPKHAB; ISSN: 0044-4618, Copyright: 2010 ACS on STN, 1958, pp. 1617-1624.

Vasserman et al., "Separation of Substances from Solutions by Chemical Precipitation. III. Automatic Control of the Process of Precipitation of Basic Nickel Carbonate in the System Ni (NO3)2-Na2CO3-H2O by the pH of the Solution", Kh. Z. Branina. Zhur. Priklad. Khim., 32, Copyright: 2010 ACS on STN, 1959, pp. 2619-2624.

Xiang et al., "Experimental Study on Synthesis of Nio Nano-Particles", Scripta Materialia, 47(4), CODEN: SCMAF7; ISSN: 1359-6462, Department of Chemical Engineering, Tsinghua University, Beijing, 100084, Peop. Rep. China, Copyright: 2010 ACS on STN, 2002, pp. 219-224.

Zhou et al., "Study of Removal of Heavy Metals from Industrial Wastewater", Zhongguo Jishui Paishui, 14(4), CODEN: ZGPAFP; ISSN: 1000-4602, Nanjing University, Nanjing, Peop. Rep. China, Copyright: 2010 ACS on STN, 1998, 17-20.

Xueyi et al. "Study on the Thermodynamic Equilibrium of the Complex System of Ni(li)-Nh3-Co32-H2o and Its Application to the Precipitation of Basic Nickel Carbonate Particles", EPD Congress 2004 as held at the 2004 TMS Annual Meeting (2004), Photomicrographs, Numerical Data, Graphs, 7 reference Published by: Minerals, Metals and Materials Society (TMS). 184 Thorn Hill Road, Warrendale, PA 15086-7528, USA Conference: EPD Congress 2004 as held at the 2004 TMS Annual Meeting, Charlotte, NC, USA, ISBN: 0-87339-565-4, Central-South University of Changsha, 410083, China.

Liu et al. "An Improved Purification Method For Preparation of Basic Nickel Carbonate Of High Purity Via Chemical Precipitation", Journal of Wuhan University of Technology (Materials Science Edition) (Jun. 2008) 23, (3), Published by: Wuhan University of Technology, 122 Luoshi Road, Wuhan, 430070, China, maito: jwtu@mail.whut.edu.cn, URL: whjtkjdxxb.periodicals.net.cn ISSN: 1000-2413, College of Chemical Engineering, Sichuan University, Chengdu, 610065, China, Copyright: 2010 CSA on STN, 2008, pp. 331-333.

Machine Translation of JP 2001-335326, Retrieved from <http://dossier.idpl.go.jp/text_trans.html> dated Mar. 11, 2013.

Sodium carbonate—SIDS Initial Assessment Report for SIAM 15, UNEP Publications, Feb. 19, 2003.

Cloutier et al. "The Study of the Precipitation of Carbonates", Proceedings and Transactions of the Royal Society of Canada, 33(III), CODEN: PTRCBI; ISSN: 0316-4616, Copyright: 2010 ACS on STN, 1936, pp. 149-164.

Guo et al., "Preparation of Basic Nickel Carbonate Particles in Solution System of Ni(II)-NH3-CO2-3-H2O", Transactions of the Nonferrous Metals Society of China (2004), vol. 14, (5), Numerical Data, Graphs, Photomicrographs, Spectra, 15 reference Published by: Nonferrous Metals Society of China, Central South University of Technology, School of Metallurgical Science and Engineering, Central South University, Changsha 410083, China, ISSN: 1003-6326, Copyright: 2010 CSA on STN, 2004, pp. 1006-1011.

Kucha et al., "Manufacture of Basic Nickel Carbonate", Issled. i Razrab. Syr'ya diya Prigot. Katalizatorov, M., From: Reference Zh., Khim., Abstract No. 12L142, Copyright: 2010 ACS on STN, 1991, pp. 41-43.

Makarov et al., "Optimization of Natural Water Purification to Remove Nickel and Copperions With Carbonate Flour", Russian Journal of Applied Chemistry (Translation of Zhurnal Prikladnoi Khimii), 74(12), CODEN: RJACEO, ISSN: 1070-4272, Tananaev Institute of Chemistry and Technology of Rare Elements and Mineral Raw Materials, Kola Scientific Center, Russian Academy of Sciences, Apatity, Russia, Copyright: 2010 ACS on STN, 2001, pp. 2045-2050.

Noguchi et al. "Research on Recovery of Valuable Metal from Plating Waste Water—(1) Recovery of Nickel by Compound Precipitation Method", Journal of the Mining and Materials Processing Institute of Japan vol. 120, (4-5), Graphs, Numerical Data, Photomicrographs, Spectra, 16 reference, Kyushu University of Technology, Copyright: 2010 CSA on STN, 2004, pp. 209-216.

(56) References Cited

OTHER PUBLICATIONS

Van Weert et al., "The Production of Nickel Carbonate Spheroids From Dilute Solutions in a Pellet Reactor", Published by: The Minerals, Metals & Materials Society. 420 Commonwealth Dr., Warrendale, Pennsylvania 15086, USA Conference: Extractive Metallurgy of Copper, Nickel and Cobalt. vol. I: Fundamental Aspects, Denver, Colorado, USA, Delft University of Technology, DHV Water, Copyright: 2010 CSA on STN, Feb. 21-25, 1993, pp. 1133-1144.

* cited by examiner

CALCINATION AND REDUCTION PROCESS INCLUDING A FLUIDIZING BED REACTOR

CROSS-REFERENCE TO RELATED APPLICATIONS

This application claims the priority filing dates of U.S. provisional application Ser. No. 61/495,784, filed Jun. 10, 2011, and of U.S. provisional application Ser. No. 61/495,789, filed Jun. 10, 2011, the disclosures of which are specifically incorporated herein by reference in their entireties.

FIELD OF THE INVENTION

Methods are described herein for the preparation of nickel metal (Ni(0)) from selected nickel(II)-containing solid compositions. The nickel so produced is reactive and readily forms a complex with phosphorus-containing ligands. The conditions used for preparation of the reactive nickel metal can be adapted to generate nickel metal with good flow characteristics and a high degree of reactivity in formation of nickel-ligand complexes useful for catalysis of hydrocyanation reactions. A fluidizing bed method can be employed, which accomplishes calcination and reduction in separate or combined steps. Thus, a bed of nickel(II)-containing solids can be fluidized with a gas capable of providing conditions for the calcination and reduction of the nickel(II) within the solids to nickel metal. The method includes a fluidizing gas which is flowing and substantially supporting the solids. The fluidizing gas can further include steam, which surprisingly facilitates production of nickel metal powders with good flow characteristics.

BACKGROUND OF THE INVENTION

Although hydrocyanation catalyst systems have been employed for a number of years, procedures for making those catalyst systems are not optimally efficient. For example, nickel metal atoms can be combined with phosphorus-containing ligands to generate hydrocyanation catalysts (see, e.g., U.S. Pat. Nos. 5,981,722, 7,629,484 and 7,470,805). However, nickel is poorly soluble, and many nickel metal preparations combine poorly with phosphorus-containing ligands. For example, when nickel is agglomerated even lower levels of nickel combine with phosphorus-containing ligands. However, even when nickel starting materials from different commercial sources are processed identically one source can provide nickel metal that optimally combines with phosphorus-containing ligands, while another source does not.

More efficient processes for making such catalysts are desirable are therefore needed, so that greater percentages of nickel preparations can be used in nickel-ligand catalyst and so that less waste is generated during catalyst preparation.

SUMMARY OF THE INVENTION

Nickel metal (Ni(0)) in forms particularly suited for use in homogeneous catalytic hydrocyanation chemistry can be prepared using the methods described herein. As illustrated herein, when nickel(II)-containing compositions are processed to nickel metal (Ni(0)) by suspending the nickel(II)-containing compositions in a gas within fluidized bed apparatus, the presence of steam surprisingly facilitates production of free-flowing nickel metal (Ni(0)) powders. When steam is not present, the resulting nickel metal (Ni(0)) can be agglomerated or formed into clumps that are difficult to handle and that do not optimally complex with phosphorus-containing ligands.

Nickel powders prepared by methods of the invention can be particularly suited for formation of catalytically active nickel-ligand complexes, wherein the ligands are phosphorus-containing, and the complexes are catalysts active in hydrocyanation reactions. Methods and compositions described herein pertain to catalyst systems for the hydrocyanation of ethylenically unsaturated compounds, for example, catalyst systems such as phosphite-nickel complexes useful to catalyze the hydrocyanation of ethylenically unsaturated compounds. Such catalyst systems are used for hydrocyanation of 1,3-butadiene (BD) to form pentenenitrile (PN) and for hydrocyanation of pentenenitriles to form adiponitrile (ADN), which are all commercially important products in the polyamide (particularly nylon) synthesis field.

One aspect of the invention is a method for the production of nickel metal (Ni(0)) from a nickel(H)-containing composition including steps of: (a) providing a nickel(II)-containing composition and a gas to a fluidizing bed reactor, wherein the gas is flowing and substantially supporting solids from the composition; and (b) reducing nickel in the nickel(II)-containing composition to thereby produce nickel metal (Ni(0)) from a nickel(II)-containing composition; wherein the composition includes nickel(II)-containing substances selected from a group consisting of: basic nickel carbonate, nickel carbonate, nickel nitrate, nickel bicarbonate, nickel oxalate, nickel formate, nickel squarate, nickel oxide and nickel hydroxide. Such starting forms of nickel salts include those that can be obtained from processing of nickel ores, such as laterite ores, an increasingly significant source of nickel and related metals.

Another aspect of the invention is a method for the production of nickel metal (Ni(0)) from a nickel(II)-containing composition including steps of: (a) providing a nickel(II)-containing composition and a gas to a fluidizing bed reactor, wherein the gas optionally includes added steam, and wherein the gas is flowing and substantially supporting solids from the composition; and (b) reducing nickel(II) in the nickel(II)-containing composition to thereby produce nickel metal (Ni(0)) from a nickel(II)-containing composition.

The methods can include calcining the nickel(II)-containing composition prior to reducing the nickel. Such a calcining step can be performed under calcining conditions. Calcining conditions generally yield a calcined product with a carbon:nickel atomic ratio of less than one. Calcining conditions include, for example, providing a gas to the fluidizing bed reactor that includes oxygen. The gas that includes oxygen can be air. Calcining conditions can also include operating the fluidized bed for a time and at a temperature sufficient for generating nickel oxide within the nickel(II)-containing composition. For example, the temperature employed for calcination can be about 200° C. to about 600° C. The time for calcination can be about 10 minutes to 6 hours.

Reducing nickel can include adapting conditions in the fluidizing bed to include reducing conditions. Reducing conditions can include operating the fluidizing bed reactor for a time and at a temperature sufficient for reducing nickel(II) in the nickel(II)-containing composition to nickel(0) metal. For example, reducing conditions can include introducing a reductant into the gas. The reductant can be any reducing agent convenient for reduction of nickel(II) to nickel(0) metal. For example, the reductant can include hydrogen. Alternatively, a reductant can include methane, carbon monoxide hydrogen or a mixture thereof. Temperatures useful for reducing nickel containing compositions to nickel metal include temperatures of about 200° C. to about 600° C., for example, 250° C. to about 350° C. The time for reduction can be about 10 minutes to about 18 hours, for example 10 minutes to 4 hours. The gas in the fluidizing bed can include about 1 to about 99 volume percent steam or, for example, about 5 to 60 volume percent steam, or about 10 to 50% volume percent steam, or about 6% to 20% steam.

The nickel(II)-containing composition can include basic nickel carbonate that is prepared by contacting nickel(II) ions dissolved in water with carbonate ions, bicarbonate ions, or a combination of carbonate ions and bicarbonate ions.

The fluidizing bed reactor can be maintained at a temperature of about 200° C. to about 600° C. for an effective amount of time to accomplish the calcination and/or reduction, for example, up to about 10 hours. In the batch, the time for calcinations and/or reductions can be as high as several weeks, and can be separated by optional storage periods. This typically allows several batches nickel metal to be generated without cooling and re-heating the reactor. For example, about 2-20 batches of the nickel(II)-containing composition can be processed in series to produce nickel metal (Ni(0)). About 2-10 or about 2-5 or about 2-4 batches of the nickel (II)-containing composition can also be processed in series to produce nickel metal (Ni(0)).

Another aspect of the invention is a method for making a complex of nickel metal and a phosphorus-containing ligand, such as a phosphorus-containing ligand disclosed herein, the method including: contacting the phosphorus containing ligand with nickel metal produced from a nickel(II)-containing composition, wherein the production of the nickel metal occurs in a fluidizing bed reactor according to a method of the invention. At least a portion of the nickel metal in the nickel complex can be produced by a method including: providing a nickel(II)-containing composition and a gas to a fluidizing bed reactor, wherein the gas is flowing and substantially supporting solids in the composition; and reducing nickel in the nickel(II)-containing composition to thereby produce nickel metal (Ni(0)) from a nickel(II)-containing composition. The gas in the fluidizing bed reactor can include steam.

For example at least a portion of the nickel metal in the nickel complex can be produced from a first nickel composition, including nickel(II), and the first nickel composition can be converted to the nickel metal in two stages, including a calcination stage followed by a reduction stage: wherein, the calcination stage includes heating the first nickel composition to remove volatile materials and thereby generate a second nickel composition including nickel(II), and the reduction stage includes reducing the second nickel composition to produce the nickel metal(0). The first nickel composition can include: a nickel(II)-containing composition including basic nickel carbonate, nickel carbonate, nickel bicarbonate, nickel oxalate, nickel formate, nickel squarate, nickel hydroxide, nickel oxide and combinations thereof. The first nickel composition can be prepared by contacting nickel(II) ions dissolved in water with carbonate ions, bicarbonate ions, or a combination of carbonate ions and bicarbonate ions. The second nickel composition can include nickel(II) hydroxide, nickel(II)oxide and combinations thereof. Heating the first nickel composition can yield a second nickel composition with a carbon:nickel atomic ratio of less than one.

BRIEF DESCRIPTION OF THE FIGURES

FIG. 2A shows the results for basic nickel carbonate sample BNC-2; FIG. 2B shows the results for basic nickel carbonate sample BNC-6; FIG. 2C shows the results for basic nickel carbonate sample BNC-8; and FIG. 2D shows the results for basic nickel carbonate sample BNC-1 (see also Table 2).

DETAILED DESCRIPTION OF THE INVENTION

Figure 1:
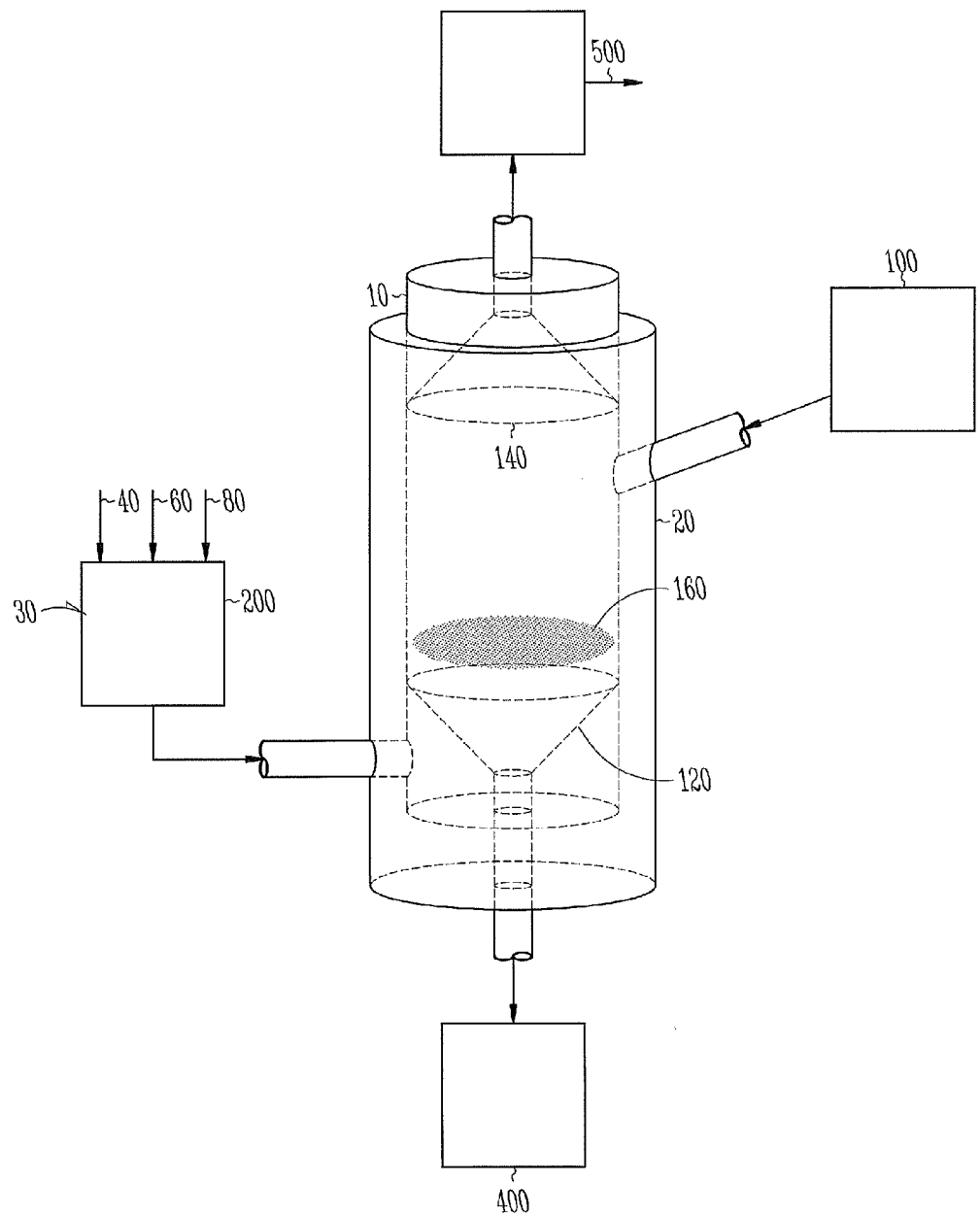
FIG. 1 is a representation of an apparatus for carrying out the methods herein disclosed.
Figure 2A:
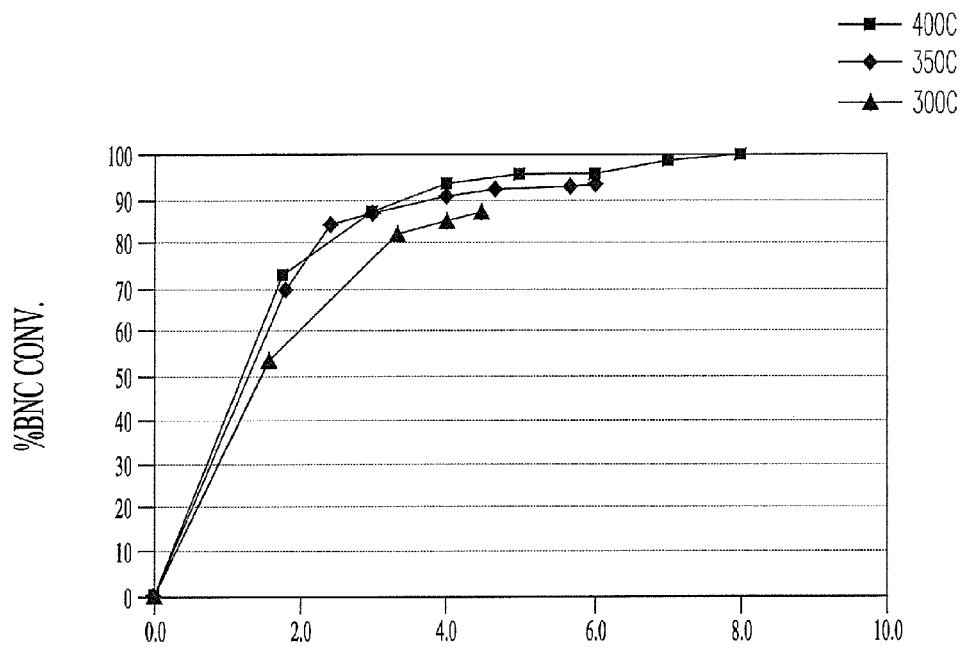
FIG. 2A-2D graphically illustrate the percent of basic nickel carbonate (BNC) from different commercial sources that is converted during calcination as a function of time. The percent BNC conversion is monitored by observing the percent of total $CO_2$ gas released at various time points.
Figure 2B:
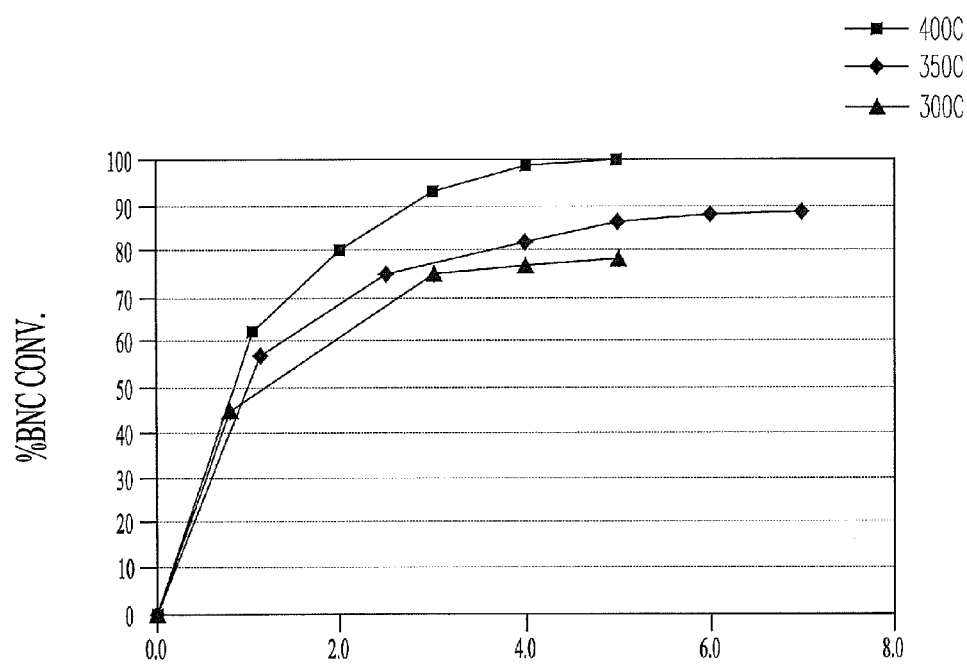
Figure 2C:
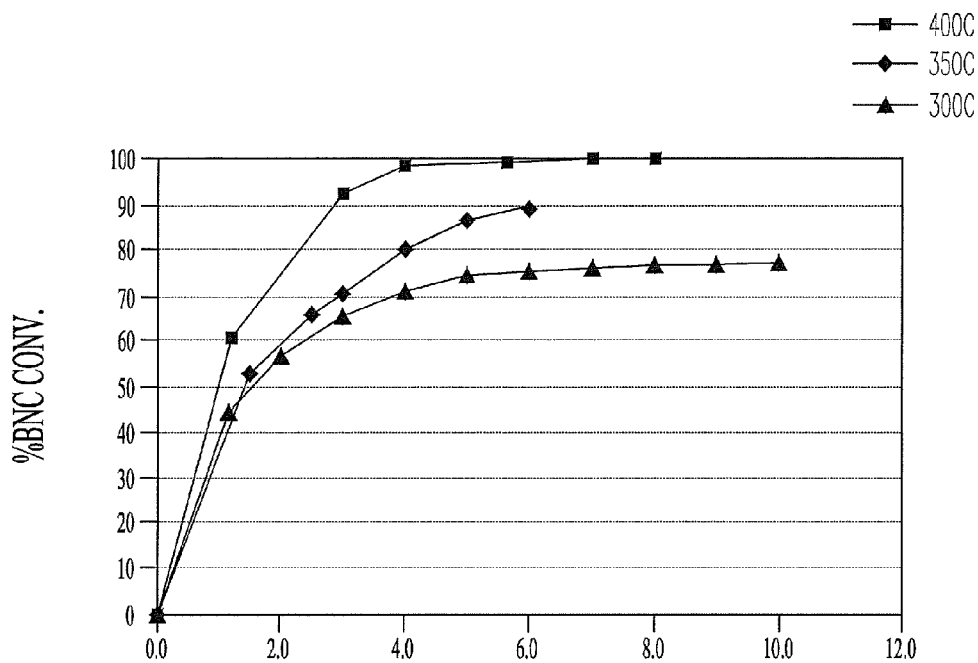
Figure 2D:
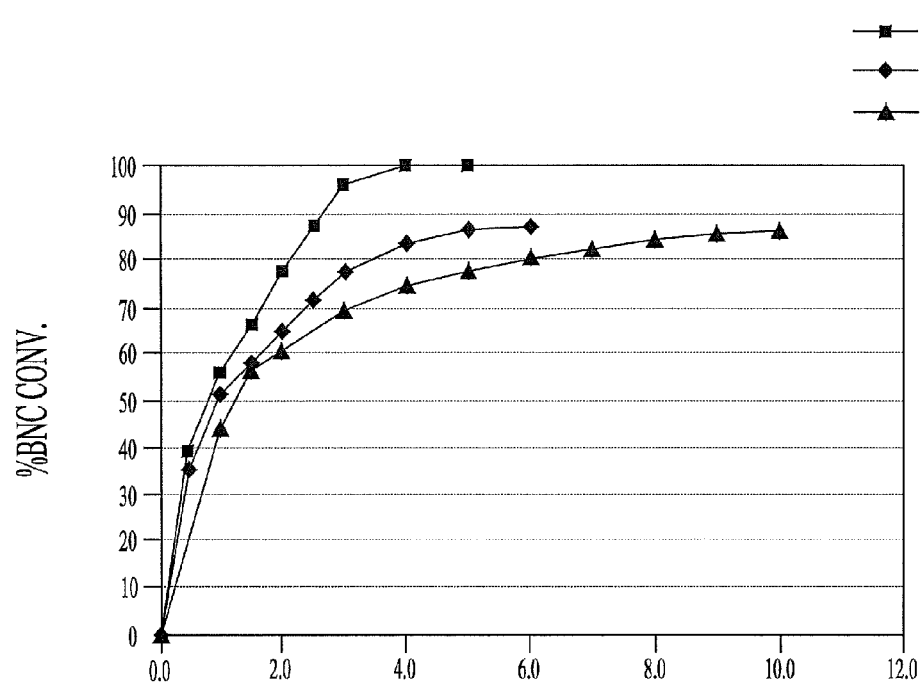

As described herein, inclusion of steam during reduction of nickel metal surprisingly generates a free-flowing, highly reactive Ni(0) powder product. Although some steam can be generated during reduction of Ni(II) to nickel metal, some reactors do not allow optimal mixing and interaction of gases during reduction of Ni(II) to Ni(0) metal. Addition of about 1% to about 50% by volume steam can facilitates production of free-flowing, highly reactive Ni(0) powder product. Alternatively, those of skill in the art can evaluate reduction conditions to assess whether optimal levels of steam are present in situ and the gases, including steam, are being optimally mixed so that free-flowing, highly reactive Ni(0) powder product is produced. Optimal levels of steam are at least about 1% by volume of the reductant gas, or at least about 2% by volume of the reductant gas. Preferably, the level of steam is at least about 5% by volume of the reductant gas, or at least about 10% by volume of the reductant gas. Hence, the steam can be generated in situ or simply added so that such optimal levels are present.

Methods are described herein for the production of nickel metal (Ni(0)) from a nickel(II)-containing composition. The nickel metal generated by the methods described herein exhibits high reactivity, such as for complex formation with phosphorus-containing ligands, and the conditions for generating this nickel metal can be adjusted to provide particulate nickel metal preparations with excellent free-flowing characteristics. Conditions that allow high rates of temperature transfer and air transfer are beneficial so that uniform reaction conditions are maintained. These nickel metal powders can be prepared by the direct reduction of nickel(II)-containing compositions with a reductant (e.g., hydrogen) at elevated temperatures, or by first calcining the nickel(II)-containing compositions and then reducing the nickel in the compositions with the reductant (e.g., hydrogen) at elevated temperatures. When steam is present, for example during the reduction process, the nickel metal so generated is free-flowing, which facilitates product removal from the reaction vessel and further processing of the nickel metal. These nickel metal preparations can then be reacted with monodentate or bidentate phosphorus containing ligands, or both, in a nitrile solvent to produce nickel complexes that can be used as homogeneous, organic-soluble catalysts for the hydrocyanation of conjugated dienes to mononitriles, and for the hydrocyanation of unsaturated nitriles to provide dinitriles, e.g., adiponitrile.

Suitable nickel(II)-containing compositions from which the nickel metal can be prepared include, for example, those selected from any of nickel oxide, basic nickel carbonate, nickel carbonate, nickel oxalate, nickel formate, nickel hydroxide and combinations thereof (also called a "first nickel(II)-containing composition"). Other possible precursors are nickel nitrate, nickel cyanate and nickel sulfate. Many nickel(II)-containing compositions are potentially useful and those which evolve carbon dioxide in a calcination step are particularly useful. The nickel(II)-containing compositions can include substantial amounts of basic nickel carbonate, nickel hydroxide, nickel carbonate, and/or nickel oxide. As used herein, basic nickel carbonate includes inorganic compounds that include nickel and carbonate, for example, compounds such as $Ni_4CO_3(OH)_6(H_2O)_4$ or simpler carbonates such as $NiCO_3$ and its hydrate ($NiCO_3(H_2O)_4$, $NiCO_3(H_2O)_6$, and the like). Basic nickel carbonate can be described with chemical formula consisting of:

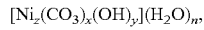

$$[Ni_z(CO_3)_x(OH)_y](H_2O)_n,$$

wherein $x=z-y/2$; $y=2\ z-2\ x$; $z=1$ to 100; and $n=0$ to 400.

The first nickel(II)-containing composition can be calcined prior to reduction. Such calcination generates a "second nickel(II)-containing composition" that includes nickel(II) oxide. When calcination is performed separately from reduction, the process is called a two step process.

As indicated above, the nickel(II)-containing compositions can also be calcined during the reduction process. Thus, the methods described herein include a one step process where calcination and reduction are performed simultaneously.

Calcination and reduction can be carried out in any suitable reactor, such as a fluid bed, an expanded fixed bed, a rotary kiln, etc. Preferably, the reactor provides uniform conditions for reduction such that the temperature is substantially uniform throughout the reactor, the reductant and steam are uniformly dispersed throughout the reactor and the nickel(II) particles are uniformly exposed to the reductant and steam. A rotary kiln may not provide such uniform conditions or such uniform exposure of the nickel to gases. However, a fluidized bed reactor typically does provide such uniform reaction conditions and also uniformly exposes suspended nickel particles to gases such as reducing gases and steam. Thus, it may be convenient to employ a fluidizing bed reactor in the methods described herein.

Thus, for example, a composition containing nickel(II)-containing solids can be charged into or placed within a fluidizing bed reactor where a gas flowing through the bed of nickel(II)-containing solids fluidizes and substantially support the solids. Flowing air, nitrogen gas, hydrogen, optionally steam, and other gases can be introduced into the reactor at the desired times and levels.

For reduction of the nickel(II) within the nickel-containing composition to generate zero valent nickel metal, the gas flowing through the bed of nickel(II)-containing solids can contain a reductant in a substantially oxygen-free gas. The reductant can be any gaseous or particulate substance that can reduce nickel(II) to nickel metal (Ni(0)). Examples of reductants that can reduce nickel(II) to nickel metal (Ni(0)) include, for example, hydrogen, methane, or carbon monoxide. Hydrogen is a convenient and inexpensive reductant.

Thus, for example, the fluidization gas can contain hydrogen in amounts sufficient to reduce at least a portion of the nickel in the fluidized nickel(II)-containing composition to nickel metal (Ni(0)).

As used herein, a substantially oxygen-free gas refers to a gas that is substantially free of molecular oxygen, $O_2$. Examples of substantially oxygen-free gases that can be employed include nitrogen, argon and neon. Deoxygenated air is another example of a substantially oxygen-free gas. Nitrogen is a convenient and inexpensive source of a substantially oxygen-free gas.

The gas used for reduction can also contain steam, which facilitates generation of a free-flowing nickel metal product. Water is released when nickel oxide is reduced with hydrogen. Hence, some steam can be generated in situ. However, hydrogen is not the only reductant that can be used for reducing Ni(II) to Ni(0) metal. Moreover, if the reactor conditions sweep the steam away from the nickel, or do not optimally expose the nickel to the steam, then the nickel can become agglomerated and difficult to process even when hydrogen is used as a reductant. Thus, added steam may not be necessary when appropriate conditions are used for producing a reactive nickel metal product, but addition of steam will prevent agglomeration and clumping of the reduced nickel product, thereby facilitating product removal from the reaction vessel and further processing of the nickel metal.

The percentage of steam in the reducing gas can be about 0.1% to 80% by volume, or about 0.1% to 70% by volume, or about 0.1% to 50% by volume, or from about 0.1% to 30% by volume. The fluidization gas can contain about 0.1% to 20% volume percent steam, or about 5% to about 20% steam. To generate useful, free-flowing nickel metal powders the reductant preferably contains more total steam per volume than hydrogen. Thus, for example, if hydrogen is used as a reductant at a volume percent of about 10%, the volume percent of steam is at least about 10.1%, or preferably the volume percent of steam is at least about 11%, or more preferably the volume percent of steam is at least about 15%. If hydrogen is used as a reductant at a volume percent of about 10%, and all of the hydrogen is converted during reduction to water, the volume percent of steam generated in situ can be about 10%. Because such in situ generation of steam depends upon the use of hydrogen and upon the particular process conditions, it is preferable to add at least 0.1% steam by volume to the reductant gas. More preferably, at least 1% steam by volume is added to the reductant gas; even more preferably, at least 5% steam by volume is added to the reductant gas, or at least 10% steam by volume is added to the reductant gas.

Prior to reduction, the fluidizing bed reactor containing the nickel(II)-containing composition (e.g., the first nickel(II)-containing solids and/or the second nickel(II)-containing solids) can be flushed with the substantially oxygen-free gas to remove molecular oxygen from the apparatus and from the nickel(II)-containing solids. The reductant or reducing agent (e.g., hydrogen gas) can then be introduced into the fluidizing gas so that a mixture of reducing agent and the substantially oxygen-free gas is used to fluidize and substantially support the solid. Reactor pressure during the reduction step is not critical. Thus, reduction can be performed at a pressure of about 0.1 atmospheres to 20 atmospheres, or at about 0.5 atmospheres to 10 atmospheres, or at about 0.5 atmospheres to 2 atmospheres. The reduction can conveniently be performed at about one atmosphere pressure. The gas flow rate during reduction is not critical and can be adjusted as desired or determined by the type of equipment used for the reduction.

Conditions sufficient to reduce a portion of the nickel(II)-containing solids to nickel metal include an elevated temperature, an amount of reducing agent (e.g., hydrogen gas) and a time sufficient to substantially reduce the nickel(II)-containing solids to form a nickel metal (Ni(0))-containing solid, i.e., a solid material that includes nickel metal (Ni(0)).

The reducing step is advantageously performed at a temperature between 200° C. and 600° C., for example, between 225° C. and 500° C., or between 250° C. and 450° C., or between 300° C. and 400° C. Reduction is typically effective using temperatures in the range of about 250° C. to about 350° C. Temperatures at the lower end of these ranges (e.g., 200° C.) can require longer reduction times. Reductions at high temperatures (e.g., 600-700° C.) can, under some circumstances or conditions, give nickel powders with low reactivity for producing the nickel-ligand catalyst complex described above. Between 250° C. and 450° C. the reduction can be carried out in a few hours, provided sufficient reducing agent (e.g., hydrogen) is passed through the reactor to substantially convert the nickel(II)-containing solids to nickel metal powder. For example, the reduction can be performed at about 250° C. to about 375° C. However, the range of temperatures that can be employed includes any numerical range representing a temperature range falling between 200° C. and 700° C. When hydrogen is used as the reducing agent, introduction of hydrogen to the fluidization reaction vessel can cause a temperature increase in the bed of nickel-containing solids, for example, of from about 10° C. to about 100° C., depending upon the concentration of hydrogen. One of skill in the art can readily adapt the conditions in the fluidization reaction vessel to accommodate variations in temperature, reductant concentration and the like.

The reducing step is advantageously performed using hydrogen as the reducing agent. For example, the reducing step can be performed for a period of at least 30 minutes using a stoichiometric excess of hydrogen. One mole of hydrogen per mole of nickel(II) in the nickel(II)-containing solid composition is the theoretical and stoichiometric amount of hydrogen required for the reducing step. The stoichiometric ratio of hydrogen to nickel, however, can vary to some extent with the temperature and time employed for reduction of the nickel. To accomplish complete conversion of the nickel(II)-containing solids to Ni(0), a stoichiometrically equal or greater amount of hydrogen can be used relative to the amount of nickel in the nickel(II)-containing solids. Using a lower concentration of hydrogen during reduction can reduce a high temperature spike that can occur when using more concentrated hydrogen. Adding hydrogen at a slower rate, or allowing the amount of hydrogen to somewhat limiting for a time, can help to regulate the temperature of the reaction. Thus, the amount of hydrogen used during reduction can vary depending upon the amount of nickel(II) that will be reduced, the temperature and the flow conditions in the reactor.

For example, the stoichiometric excess of hydrogen can be about 1.5 moles hydrogen to 1.0 mole of nickel, or about 2.0 moles hydrogen to 1.0 mole of nickel, or about 3.0 moles hydrogen to 1.0 mole of nickel, or about 4.0 moles hydrogen to 1.0 mole of nickel, or molar ratios falling between these integral molar ratio values. Or, the molar ratio of hydrogen to nickel can be in excess of 4.0 moles hydrogen to 1.0 mole of nickel. For example, when the reducing period is 1 to 2 hours a two-fold or more stoichiometric excess of hydrogen to nickel can be employed. The amount of nickel(II) in the nickel(II)-containing compositions (e.g., the first nickel(II)-containing solids or the second(II)-nickel containing solids) can be determined by a metal analysis using methods known to the skilled person. The amount of hydrogen introduced into the reduction apparatus can be varied by varying the ratio of hydrogen in the fluidizing gas relative to the substantially oxygen-free gas.

The hydrogen is therefore provided in amounts and under conditions sufficient to reduce at least a portion of the nickel (II)-containing solids to nickel metal. The percentage of hydrogen in the fluidization gas used during reduction can be about 3% to 95% by volume, or about 4% to 70% by volume, or about 5% to 50% by volume, or about 6% to 40% by volume, or about 7% to 25% by volume, or about 8% to 20% by volume, or about 9% to 15% by volume, or about 8% to 20% by volume. The amount of hydrogen employed can therefore vary. The remainder of the fluidization gas used during reduction includes substantially oxygen-free gas and, optionally, steam. Preferably, the reducing gas includes steam.

The percentage of steam in the reducing gas can be about 1% to 80% by volume, or about 1% to 60% by volume, or about 1% to 50% by volume, or about 2% to 30% by volume, or about 5% to 20% by volume. One example of a effective gas composition for reduction gas includes about 20% steam, about 20% hydrogen, and about 60% nitrogen, by volume percent. Another example of a effective gas composition for reduction gas includes about 10% steam, about 10% hydrogen, and about 80% nitrogen, by volume percent. Gas flow rate during the process is less of control variable and can be determined by the type of equipment used for the reduction and is within the knowledge of the skilled person to choose.

Reduction is generally performed for about 10 minutes to about 10 hours, or from about 0.5 hours to about 8 hours, or from about 0.5 hours to about 6 hours, or from about 0.75 hours to about 4 hours. Such time periods can be sufficient to simultaneously calcine and reduce the nickel(II)-containing solids. The reduction (and, optionally, the calcination) can be performed for about 1 hour to about 5 hours, or in about 1 hour to about 3 hours.

After reduction, the flow of hydrogen is terminated. The fluidization reactor can be flushed with substantially oxygen-free gas to remove residual hydrogen. Steam can be used during this hydrogen-removal phase. The nickel metal (Ni (0))-containing product is stored in a vacuum or in a substantially oxygen-free gas. The nickel metal produced by the reduction step can be stored under inert atmosphere, such as nitrogen or argon atmosphere, until use.

The amount of nickel metal generated and its purity can be determined by a metal analysis using methods known to the skilled person. Similarly, the amount of nickel in any of the nickel-containing compositions or solids used in the methods described herein can be determined by a metal analysis using methods known to the skilled person.

A first calcination step can be applied to a nickel(II)-containing, followed by a second step of reduction, which is applied after the calcination step.

Although nickel(II)-containing solids can be reduced to nickel metal (Ni(0)) in one step, it may be useful to calcine the nickel-containing compositions prior to reduction. As used herein "calcine" or "calcining" or "calcination" is a thermal treatment process applied to nickel(II)-containing compositions in order to bring about a thermal decomposition, phase transition, or removal of a volatile fraction. Calcination can be performed using any available calcination procedure or apparatus.

In general, such a calcination step is carried out using conditions sufficient to calcine the nickel containing solids. The calcination can be performed under conditions sufficient to substantially remove volatile materials. Such volatile materials include carbon dioxide, nitrate, nitric acid, formate, formic acid, cyanate, hydrogen cyanide, sulfate, sulfuric acid, water and the like. For example, carbon dioxide or carbon dioxide and water can be the major volatile materials that are removed, particularly when the nickel(II)-containing composition is basic nickel carbonate. The calcination can be performed under conditions sufficient to convert nickel(II)-containing solids substantially into nickel(II) oxide (NiO).

Calcination can be carried out in any suitable reactor, such as a fluid bed reactor, an expanded fixed bed, a rotary kiln, a rotary pan and such equipment known to the skilled person. It can be convenient to perform calcination of nickel(II)-containing solids in a fluidized bed apparatus so that the material can then be reduced in the same fluidized bed apparatus pursuant to the methods described herein.

The conditions within the fluidizing bed reactor are adapted to calcine the nickel-containing compositions. Generally, calcination can be carried out in any gas or atmosphere that does not react with nickel-containing salts or compound to form undesirable nickel-containing materials. Suitable convenient gases for the calcination step include air and nitrogen; others can include argon and helium. The gas or atmosphere can also contain oxygen. Air is therefore conveniently used during many calcination procedures. Thus, conditions sufficient to calcine nickel-containing solids, salts and compounds within the composition include a fluidizing gas that contains oxygen (e.g., air). Steam (gaseous water or water vapor) can be present during the calcinations step, as an option.

Temperatures useful for calcination of nickel(II)-containing compositions include those in the range of about 200 to 600° C. Below 200° C. the calcination can be incomplete, and unreacted nickel precursor can remain in the product. Above 600° C. an excessive collapse or sintering of the nickel oxide may occur under some conditions, consequentially reducing the reactivity of the nickel power product. The time for optimal calcination varies inversely with the temperature: when lower temperatures are used (e.g., 250° C.) calcination can be performed for longer time periods (e.g., up to 18-20 hours). However, when calcination is performed at temperatures of about 300° C. to 600° C., a shorter time period is effective for calcination, for example, about 10 minutes to about 6 hours, or about 10 minutes to 4 hours. The time for the calcination step can range from tens of seconds at 600° C. to multiple hours at 200° C. In general, calcination of nickel(II)-containing composition is complete within about 30 minutes to 2 hours when using temperatures of about 300° C. to 600° C. Especially desirable calcinations temperatures are from about 300° C. to about 400° C. At temperatures between 300° C. and 400° C., calcination is substantially complete within about 1 hour.

Effective calcination can be monitored and detected by observing the release of carbon dioxide from the nickel(II)-containing composition and/or by observing the conversion of nickel(II)-containing salts and compounds within the composition to nickel oxide (and/or nickel hydroxide).

After calcination is completed, the flow of oxygen-containing gas is terminated and the apparatus can be flushed with a non-oxygen-containing or inert gas. Nitrogen is useful for this purpose but other non-oxygen-containing or inert gases can also be used (e.g., argon or neon). The flow of the non-oxygen containing or inert gas is continued until oxygen is substantially removed from the reactor bed of the fluidized bed apparatus. The reduction of nickel in the calcination product can then be performed.

A fluidizing bed reactor can be employed to perform the steps of calcination and reduction of the nickel(II)-containing precursor composition to nickel metal (Ni(0)) powder. The applicants contemplate that the nickel containing precursor is first charged to a fluidizing bed reactor. Any available fluidizing bed reactor can be employed.

One example of a fluidizing bed reactor is represented schematically according to FIG. 1. In this figure, the reactor 10 can be used to suspend, calcine and reduce nickel containing solids 160. A heating mantle 20 is substantially concentrically disposed about reactor 10. Nickel(II)-containing solids 160 are provided to the reactor 10 by a fluidized bed charging means 100, for example, a gravimetric feed or a rotary type feeder. A fluidizing gas is supplied to reactor 10 by means of a gas mixer 200. The gas mixer can incorporate a gas preheating, flow control and measurement means used in the art. The fluidizing gas can include air, de-oxygenated air (e.g., nitrogen), hydrogen and steam supplied via a manifold in fluid communication with the gas mixer 200 via input ports 30, 40, 60, and 80; respectively. The fluidizing gas passes into reactor 10 and is distributed by means of a perforated gas distributor 120. The fluidizing gas can be preheated in the gas mixer 200 and further brought to the temperature desired in the reactor 10 as the gas is passed through a portion of the heating mantle 20. The heated fluidizing gas supports the nickel(II)-containing solids 160 in the reactor 10. A filter means 140 permits passage of the fluidizing gas as it exits the reactor 10 and passes into fine solid separator 300 which is adapted to remove fine solids from the fluidizing gas. The fluidizing gas can be recirculated via the gas recycler 500 back to the gas mixer 200 for heating and optional recharging with reducing gas. Product can be recovered by means of a port centrally located in the gas distribution means 120. This port being substantially in fluid communication with the product collection means 400.

For example, a closed reactor is provided with flowing air and the temperature is raised to the desired calcination temperature, for example, about 200° to 700° C. At the calcination temperature of 300° C. or higher, with air passing through the reactor for a period of about 1 hour, the nickel (II)-containing composition is substantially converted to nickel oxide. Following the calcination step, reactor is purged with a nitrogen atmosphere for a sufficient time to remove substantially all oxygen. Upon introduction of hydrogen an immediate temperature increase of about 10° C. is measured within the bed of nickel oxide in the reactor. Effective gas concentrations are 20% steam, 20% hydrogen, 60% nitrogen; all by volumetric measurement. The time period observed at the elevated bed temperature can correspond to the time required to add the stoichiometric amount of hydrogen which reduces the nickel oxide to nickel metal. The nickel metal powder in the reactor is cooled in an atmosphere substantially free of oxygen and shown to exhibit ferromagnetism.

It may be advantageous to manufacture a series of batches of nickel metal in a sequential manner so that the reactor does not cool between batches. Such a manufacturing practice is efficient and saves the energy needed to re-heat the reactor between batches. Thus, a number of batches of nickel metal can be manufactured in series. For example, up to about 10 or 20 batches of nickel metal can be made at one time. It is generally preferable that at least two batches of nickel metal be made at one time. More preferably, about 2 to about 6 batches of nickel metal are made at one time. For example, it is convenient to make about 3 batches of nickel metal at one time.

Basic nickel carbonate (BNC) can be employed as or can be included within the nickel(II)-containing composition that is processed to generate nickel metal. Basic nickel carbonate is available commercially. For example, basic nickel carbonate can be obtained from MetChem Corporation, an American distributor of this material. According to the vendor, the basic nickel carbonate provided is produced by precipitating the basic nickel carbonate from an aqueous solution including nickel, ammonia, ammonium carbonate, and water. According to the vendor, the basic nickel carbonate is produced from an ore including nickel and the basic nickel carbonate and this material can further include at least one element selected from the group consisting of aluminum, calcium, cobalt, copper, iron, magnesium, manganese, sodium, sulfur, and zinc. One sample had a chemical analysis shown in Table 1.

TABLE 1

Analysis of MetChem Basic Nickel Carbonate Powder.
Nickel 47% by weight

| Cobalt 65 ppm | Copper 20 ppm | Iron 55 ppm | Zinc 12 ppm |
|---|---|---|---|
| Magnesium 60 ppm | Calcium 60 ppm | Sodium 60 ppm | Sulfur 175 ppm |

It may be desirable to manufacture the basic nickel carbonate rather than obtaining it from a commercial source. For example, as illustrated herein, different commercial sources of basic nickel carbonate can have different fluidization properties and can require different calcination and/or reduction conditions. Moreover, impurities can be avoided and the composition of the basic nickel carbonate can be controlled by manufacture of the basic nickel carbonate using selected reactants and manufacturing conditions.

Suitable basic nickel carbonates can therefore also be produced by precipitating the basic nickel(II) carbonate from an aqueous solution including nickel(II), carbonate anion, and water. For example, basic nickel carbonate can be produced by precipitating it from at least one aqueous solution selected from the group consisting of (1) an aqueous solution including nickel(II), ammonia, ammonium carbonate, and water; (2) an aqueous solution including nickel(II), carbonate anions, and water; and (3) an aqueous solution including nickel(II), bicarbonate anions, and water.

Basic nickel carbonate compositions can be made by adding a precipitant solution to a nickel solution in a precipitation reactor to form a reaction mixture; and precipitating a nickel composition from the reaction mixture, wherein the nickel solution includes nickel(II) ions and water. The precipitant solution can be selected from the group consisting of: (a) bicarbonate ions and water, (b) carbonate ions and water, and (c) mixtures thereof. The mole ratio of bicarbonate ions to nickel ions in the reaction mixture after adding the precipitant solution can range from 0.1:1 to 2:1, including from about 0.5:1 to about 1.6:1, from about 0.5:1 to about 1.2:1, from about 1.0:0 to about 1.9:1, from about 1.2:1 to about 1.9:1, from about 0.8:1 to about 1.4:1, from about 1.0:1 to about 1.8:1, from about 1.0:1 to about 1.6:1, from about 1.0:1 to about 1.4:1, from about 0.8:1 to about 1.4:1, and from about 0.8:1 to about 1.2:1. The mole ratio of carbonate ions to nickel ions in the reaction mixture after adding the nickel solution can range from 0:1 to 1.6:1, including from about 0:1 to about 1.4:1, from about 1.0:0 to about 1.2:1, from about 0.8:1 to about 1.4:1, from about 1.0:1 to about 1.6:1, from about 1.0:1 to about 1.6:1, from about 1.0:1 to about 1.4:1, from about 0.8:1 to about 1.4:1, and from about 0.8:1 to about 1.2:1. Blends of bicarbonates and carbonates can also be used in the precipitant solution. Further information on preparing and using basic nickel carbonate is available in PCT/US2010/060388, filed Dec. 15, 2010 and published as WO/2011/075496, and in PCT/US2010/060381, also filed on Dec. 15, 2010 and published as WO/2011/075494, which are both specifically incorporated herein by reference in their entireties.

The precipitation reactor can be any suitable containment vessel such as a tank or pipe. The reaction mixture can also be agitated prior to and/or during the precipitation of the basic nickel carbonate. For example, agitation can be done by mechanical stirring, pumped circulation loop, flow-through static mixture, or ultrasound. The basic nickel carbonate can be precipitated within a temperature range of from about 0° C. to about 90° C., including from about 20° C. to about 90° C., from about 20° C. to about 70° C., from about 20° C. to about 50° C., from about 50° C. to about 90° C., from about 60° C. to about 80° C., and from about 65° C. to about 75° C. Furthermore, the basic nickel carbonate can be precipitated from the reaction mixture in the presence of added carbon dioxide. For example, the carbon dioxide can be added to the precipitation reactor, added to the nickel solution, added to the precipitant solution, added to the reaction mixture, and any combination thereof. Also, the precipitant solution can be fed over a period of from about 30 minutes to about 60 minutes, and can be done in a semi-continuous or continuous manner. Further, the precipitant solution can be added to the nickel solution in the precipitation reactor in a semi-continuous or continuous manner, for example, by gradual addition.

The reaction mixture can also be digested after contacting the precipitant solution to the nickel solution by heating the reaction mixture from between about 50° C. and about 90° C. for a period of from about 10 minutes to about 24 hours. Other suitable temperature ranges include from about 60° C. to about 80° C. and from about 65° C. to about 75° C. Other suitable time periods can range from about 0.5 hours to about 20 hours, including from about 0.5 hours to about 14 hours, from about 1 hour to about 10 hours, from about 1 hour to about 6 hours, and from about 1 hour to about 2 hours.

The methods for making basic nickel carbonate can further include, after the precipitation step, washing the precipitated basic nickel carbonate with water; and partially drying the precipitated basic nickel carbonate. For example, the precipitated basic nickel carbonate from the reaction mixture can be separated from the reaction mixture by filtration or decantation, the resulting precipitated basic nickel carbonate can be washed with water by filtration or decantation, and the resulting precipitated basic nickel carbonate can be dried by water evaporation between 60° C. and 100° C. Drying can be performed under ambient pressure or under vacuum, and in the presence of an inert gas such as nitrogen.

The nickel solution, including nickel(II) ions and water, can be prepared by dissolving a nickel(II) salt in water. The nickel salt can be any salt that is soluble in water, for example $NiCl_2$, $NiSO_4$, and $Ni(NO_3)_2$. The precipitant solution, including bicarbonate ions, can be prepared by dissolving a bicarbonate salt, for example, $NaHCO_3$ and $NH_4HCO_3$, in water or the precipitant solution can be prepared in-situ by dissolving $CO_2$ and an alkali metal hydroxide or ammonia in water. Likewise, the precipitant solution, including carbonate ions, can be prepared by dissolving a carbonate salt, for example $Na_2CO_3$ or prepared in-situ by dissolving $CO_2$ and an alkali metal hydroxide in water by available methods. The anion of the nickel salt and cation of the bicarbonate or carbonate salt can be selected such that a salt produced from the precipitation, including both the cation and anion from the reaction mixture (for example NaCl), is soluble in the water of the reaction mixture. Such a selection provides a method for separating the salt product from the precipitated nickel composition.

A highly pure basic nickel carbonate with predictable and substantially uniform fluidization, calcination and reduction properties can therefore be produced. Such a highly pure basic nickel carbonate is readily reduced to generate a substantially pure nickel preparation. The nickel preparation is preferably zero-valent nickel (Ni(0)). The basic nickel carbonate can be substantially free of other metals (e.g., without aluminum, zinc, tungsten and/or iron) and anions other than carbonate, oxygen and/or hydroxide. The nickel preparation can be isolated without, or be substantially free of, an associated ion (e.g., without an anion) or other metal (e.g., without aluminum, tungsten and/or iron). The nickel preparation can also be substantially free of carbon-containing, silicon-containing and/or nitrogen-containing moieties and/or compounds.

The basic nickel carbonate and other nickel sources for preparing nickel (e.g., basic nickel carbonate, nickel carbonate, nickel bicarbonate, nickel oxalate, nickel formate, nickel squarate, nickel oxide and nickel hydroxide) can be substantially free of sodium, calcium, potassium, and/or other alkali metals and/or alkaline earth metals. For example, the basic nickel carbonate and/or nickel preparation can have less than 10% impurities, or less than 7% impurities, or less than 5% impurities, or less than 4% impurities, or less than 3% impurities, or less than 2% impurities. In general, smaller percentages of impurities are desirable such as less than 1% impurities, or less than 0.7% impurities, or less than 0.6% impurities, or less than 0.5% impurities, or less than 0.4% impurities, or less than 0.3% impurities, or less than 0.2% impurities, or less than 0.1% impurities, or less than 0.07% impurities, or less than 0.05% impurities, or less than 0.03% impurities, or less than 0.01% impurities.

Such a nickel preparation can be combined with a phosphorus-containing ligand, for example, any of those described herein. The preparations of nickel metal powders described herein, when contacted with suitable phosphorus containing ligands, provide organophosphorus-based nickel catalysts effective for use in hydrocyanation chemistry. Steam is useful to generate a free-flowing nickel metal powder product. The freely flowing nickel metal (Ni(0)) powder generated by methods described herein is reactive and useful for making catalysts containing suitable phosphorus containing ligands.

The nickel metal powder generated as described herein can be used to produce an organophosphorus nickel catalyst useful in hydrocyanation chemistry, such as in the homogeneous catalytic reaction of hydrogen cyanide with 1,3-butadiene. For example, processes to provide the organophosphorus nickel catalyst can involve contacting the nickel metal powder (e.g., generated as described herein) with a phosphorus containing ligand in an organonitrile solvent, optionally in the presence of a Lewis acid. The phosphorus containing ligand can be monodentate, e.g. tri-tolylphosphite, or a bidentate ligand. The monodentate ligand can require a catalyst, such as di-tolyl-chloro-phosphite, to catalyze the formation of the organophosphite nickel complex. The bidentate ligand can require the addition of a Lewis acid, e.g. zinc chloride, for efficient formation of the organophosphite nickel complex. Thus, for example, the nickel powder can be contacted with the ligand, such as a ligand dissolved in an organonitrile solvent or other organic solvent, with a Lewis acid such as zinc chloride. The solution can be mixed in an agitated slurry reactor at a temperature of about 5° C. to about 60° C. to 120° C. The nickel complex so-produced is an effective hydrocyanation catalyst.

The phosphorus-containing ligand can be selected from the group consisting of a bidentate phosphite, a bidentate phosphonite, a bidentate phosphinite, a bidentate phosphine, and a mixed bidentate ligand; wherein the mixed bidentate ligand is selected from the group consisting of a phosphite-phosphonite, a phosphite-phosphinite, a phosphite-phosphine, a phosphonite-phosphinite, a phosphonite-phosphine, and a phosphinite-phosphine.

The phosphorus-containing ligands are chemically bonded to nickel as complexes, where the nickel includes zero-valent nickel. Some levels of free phosphorus-containing ligands, not bonded to said complexes, can be present such as monodentate or multidentate ligands, for example bidentate or tridentate ligands. The term "bidentate" means that the ligand contains two phosphorus atoms per ligand molecule, and both phosphorus atoms of the ligand are bonded to a single metal atom. The term "tridentate" means the ligand contains three phosphorus atoms per ligand molecule, and the three phosphorus atoms of the ligand are bonded to a single metal (e.g., nickel) atom. The phosphorus-containing ligand can be a single compound or a mixture of compounds. The phosphorus-containing ligand can be selected from the group consisting of a phosphite, a phosphonite, a phosphinite, a phosphine, and a mixed P-containing ligand or a combination of such members.

An example of a bidentate phosphorus-containing ligand that can be employed is represented by Formula I.

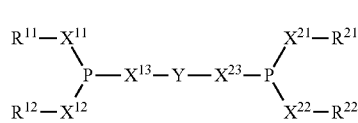

Formula I wherein, $X^{11}, X^{12}, X^{13}, X^{21}, X^{22}, X^{23}$ independently represent oxygen or a single bond; $R^{11}, R^{12}$ independently represent identical or different, single or bridged organic radicals;

$R^{21}, R^{22}$ independently represent identical or different, single or bridged organic radicals; and Y represents a bridging group.

It is to be understood that Formula I can represent a single compound or a mixture of different compounds, each having the indicated formula.

Monodentate phosphorus-containing ligands can be selected from the group consisting of a monodentate phosphite, a monodentate phosphonite, a monodentate phosphinite, and a monodentate phosphine.

The Lewis acid can be selected from the group consisting of inorganic compounds, organic compounds, and organometallic compounds. For example, the Lewis acid can include at least one chemical element selected from the group including scandium, titanium, vanadium, chromium, manganese, iron, cobalt, copper, zinc, boron, aluminum, yttrium, zirconium, niobium, molybdenum, cadmium, rhenium, lanthanum, europium, ytterbium, tantalum, samarium, and tin. A Lewis acid can, for example, be selected from the group consisting of zinc chloride, ferrous chloride, or a combination of zinc chloride, ferrous chloride and mixtures thereof. For example, the Lewis acid can be zinc chloride.

The organonitrile can be a pentenenitrile is selected from one or more members of the group consisting of 2-pentenenitrile, 3-pentenenitrile, 4-pentenenitrile, 2-methyl-3-butenenitrile, and 2-methyl-2-butenenitrile. Such an organonitrile can be used as the solvent when generating the catalyst (where the catalyst is a complex between nickel metal and a phosphorus containing ligand).

Although the foregoing detailed description contains many specifics for the purpose of illustration, a person of ordinary skill in the art will appreciate that many variations and alterations to the following details are within the scope of the invention.

Aspects of the present disclosure employ, unless otherwise indicated, techniques of chemistry, and the like, which are within the skill of the art. Such techniques are explained fully in the literature. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Unless indicated otherwise: parts are parts by weight, concentration in % is % by volume (or sometimes by weight percent, "wt %"), temperature is in ° C., and pressure is in atmospheres. Pressures reported in pounds per square inch gauge (psig) include the pressure of one atmosphere (14.7 pounds per square inch). One atmosphere is equivalent to 14.7 pounds per square inch absolute or 0 pounds per square inch gauge. Standard temperature and pressure are defined as 25° C. and 1 atmosphere.

Herein the terms calcination or calcining are used as the skilled person would understand their meaning. That is, a thermal process applied to substantially solid phase material which ultimately induces decomposition, change of phase or structure and the evolution of a volatile component.

The following Examples demonstrate the present invention and its capability for use. Several details and features are capable of modification in various apparent respects, without departing from the scope and spirit of the present invention. Accordingly, the Examples are to be regarded as illustrative in nature and non-limiting.

The Examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for.

EXAMPLES

In the following examples a bidentate phosphite ligand, Ligand A, is used in assays to evaluate ligand complex formation by various nickel preparations.

Ligand A can be prepared by any suitable synthetic means known in the art. For example, 3,3'-diisopropyl-5,5',6,6'-tetramethyl-2,2'-biphenol is prepared by a procedure disclosed in U.S. Published Patent Application No. 2003/0100802 in which 4-methylthymol can undergo oxidative coupling to the substituted biphenol in the presence of a copper chlorohydroxide-TMEDA complex (TMEDA is N,N,N',N'-tetramethylethylenediamine) and air. The phosphorochloridite of 2,4-xylenol, [$(CH_3)_2C_6H_3O]_2PCl$, can be prepared by a procedure disclosed in U.S. Published Patent Application No. 2004/0106815. The procedure provides a selective formation of phosphorochloridite from anhydrous triethylamine and 2,4-xylenol, which are added separately and concurrently in a controlled manner to $PCl_3$ dissolved in an appropriate solvent under temperature-controlled conditions. The reaction of this phosphorochloridite with the 3,3'-diisopropyl-5,5',6,6'-tetramethyl-2,2'-biphenol to form the desired Ligand A can be performed, for example, according to the method disclosed in U.S. Pat. No. 6,069,267. The phosphorochloridite when contacted with 3,3'-diisopropyl-5,5',6,6'-tetramethyl-2,2'-biphenol in the presence of an organic base provides Ligand A. This ligand is isolated according to techniques known in the art, for example as also described in U.S. Pat. No. 6,069,267. Ligand A is an example of a compound of Formula I (vide supra).

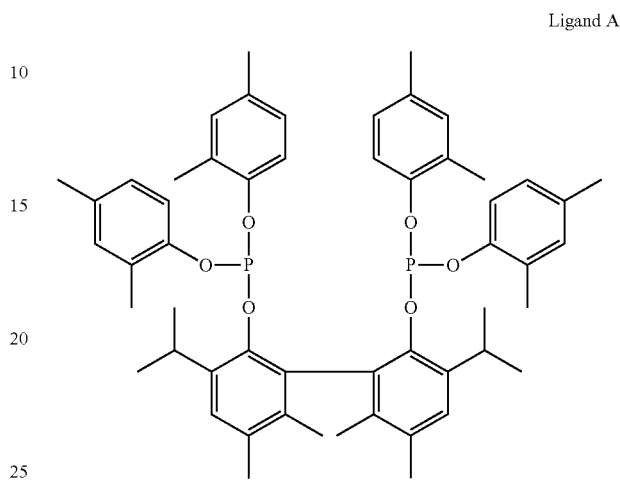

Ligand A

Additional bidendate ligands, ligand complexes, and methods of making such ligands and complexes, are disclosed in U.S. Pat. No. 6,171,996, herein incorporated by reference in its entirety.

In the following examples the reactivity of nickel metal samples is expressed as an activity. Such an activity can be expressed as a measure of the reactivity of the nickel metal samples relative to a standard reactivity. However, higher activities are indicative of a faster reaction rate to form the soluble nickel-ligand complex.

Basic nickel carbonate (BNC) can be converted directly to nickel metal with hydrogen at elevated temperatures, referred to hereinafter as the one step process. Alternatively, a first calcination step is applied to the BNC at elevated temperature with the formation of nickel oxide (NiO). A second step involving reduction with hydrogen at elevated temperatures provides nickel metal. Hereinafter, calcination followed by reduction is referred as the two step process. Both methods are able to provide a reactive nickel metal.

In all of the following examples, calcinations are carried out in a muffle furnace using air as the calcination atmosphere. Reductions are all carried out in an electrically heated tubular fluidized bed reactor using flowing hydrogen as a reducing gas.

The basic nickel carbonate (BNC) used in examples 1-25 is obtained from Konigswarter & Ebell, Chemische Fabrik GmbH, Im Ennepetal 19-21, D-58135 Hagen, Germany.

To evaluate the ability of nickel preparations to form complexes with phosphorus-containing ligands, the procedure is generally as follows: a reactor bottle is charged with 80 gram of a 5% by weight Ligand A solution in 3-pentenenitrile (3PN) solvent, 3.2 gram of the nickel metal (Ni(0)), and 0.5 gram of anhydrous $ZnCl_2$. After heating the reaction mixture in the bottle is to 60° C., filtered liquid samples are withdrawn as a function of time and analyzed for soluble nickel concentration. The activity of the nickel is determined by measuring the concentration of soluble nickel complex as a function of time by chemical analysis.

An empirical rate equation for Ni dissolution in catalyst-preparation assay is employed to provide a numerical value indicative of nickel activity (ability to become a soluble catalyst complex with Ligand A in the following reaction:

Ni+Ligand $A(A)$+ZnCl2$(B)$+3$PN$↔Catalyst$(C)$

The following equation describes the rate of Nickel-Ligand A catalyst formation:

$r=a*k'*w_{Ni}*C_A^{a'}*C_B^{b}*[1-C_C/(Keq*C_A*C_B)]*2*(C_A/C_{A0})/[1+(C_A/C_{A0})]$ where:
 a=activity of nickel
 $w_{Ni}$=weight loading of nickel (weight of nickel/weight of solution)
 k'=Arrhenius rate constant:

[(mmoles Ni/liter)^0.5/hr]=1.539×10^10 exp[−6832.1/T(K)]

$C_A$=concentration of Ligand A (mmol/L)
 $C_{A0}$=Initial concentration of Ligand A (mmol/L)
 $C_B$=concentration of ZnCl$_2$ (mmol/L)
 a'=order of reaction with respect to Ligand A=0
 b=order of reaction with respect to ZnCl$_2$=0.5
 Keq=equilibrium constant for the chemical reaction

[liters/mmol]=exp[11555/T(K)−35.231]

T=temperature in degrees Kelvin.

It is assumed that the 3-pentenenitrile is in far excess so its order of reaction with respect to the rate of 3-pentenenitrile dissolution is considered zero. The order of reaction with nickel loading is considered to be 1.

The rate constant k' is defined for a standard MetChem BNC reduced at 400° C. under pure hydrogen to nickel. However, to account for other sources of nickel that can have different in properties, a factor is applied that is termed the activity of nickel dissolution. The 'activity' number was chosen to be 1 for the specific condition of MetChem BNC reduced at 400° C. to nickel, dissolved at 80° C. in the catalyst-preparation solution with ZnCl$_2$/Ligand A molar ratio of 0.8 and 4 wt % nickel loading, where dissolution is at a rate of 980 ppm Ni/hr. In principle, a higher activity is essentially a higher rate constant specific to a given nickel. In order to move away from separately determining rate constant for each type of nickel, the activity term is defined to get around this issue.

Note that if recrystallized Ligand A is employed in the assay, the measured nickel activity is higher than if an extracted (e.g., recycled) Ligand A preparation is employed. The difference in activity is about 2-fold.

Examples 1 to 4

In a series of experiments BNC is reduced directly in hydrogen flowing at 0.5 liters/min at temperatures between 200° C. and 500° C. The reduction process at 200° C. is conducted for 6 hours. At all other temperatures, a reduction time of 2 hours is used. The activities of the nickel metal samples are as follows:

|  | Example | | | |
|---|---|---|---|---|
|  | 1 | 2 | 3 | 4 |
| Temperature (° C.) | 200 | 300 | 400 | 500 |
| Activity | 5.1 | 6.4 | 4.3 | 2.5 |

The results indicate a maximum activity is obtained for the direct reduction of BNC at 300° C.

Examples 5 to 8

In a series of experiments, BNC is first calcined in air using a muffle furnace at temperatures between 200° C. and 500° C. The calcination at 200° C. is carried out for a period of 18 hours. At all other temperatures, calcinations are conducted for 1 hour. The sample calcined at 200° C. contains some unreacted BNC, whereas the BNC calcined at the higher temperatures contains no residual BNC. The nickel oxide formed during calcination is subsequently reduced in hydrogen flowing at 0.5 liters/min at the same temperature as is used for calcination (e.g. BNC calcined at 300° C. is reduced at 300° C.). At 200° C. the reduction step is conducted for 6 hours. A reduction time of 2 hours is used at all the other temperatures. The activities of the nickel metal samples are as follows:

|  | Example | | | |
|---|---|---|---|---|
|  | 5 | 6 | 7 | 8 |
| Temperature (° C.) | 200 | 300 | 400 | 500 |
| Activity | 8.2 | 8.3 | 5.4 | 1.7 |

These activities suggest that the reactivity of the nickel metal toward formation of the soluble nickel complex declines as temperatures rise above 300° C. Since there is undesired residual BNC in the sample prepared at 200° C., calcination and reduction at 300° C. can be an optimal combination of temperatures using the types of equipment employed. It is observed that the activity achieved at 300° C. is greater for the single step process.

Examples 9 to 16

This series of experiments is designed to illustrate an optimal reduction temperature for nickel oxide prepared by calcination of BNC in air at 300° C. The BNC is first calcined for 1 hour in air using a muffle furnace at a temperature of 300° C. The nickel oxide so-formed by calcination contained no residual BNC, as determined by infrared analysis. The nickel oxide formed during calcination is subsequently reduced in hydrogen flowing at 0.5 liters/min at temperatures from 150° C. to 600° C. The reduction is carried out for 6 hours at 150° C., 4 hours at 200° C. and 250° C., while a reduction time of 2 hours is employed at all the other temperatures. The activities of the nickel metal samples are as follows:

|  | Example | | | | | | | |
|---|---|---|---|---|---|---|---|---|
|  | 9 | 10 | 11 | 12 | 13 | 14 | 15 | 16 |
| Temperature (° C.) | 150 | 200 | 250 | 300 | 350 | 400 | 500 | 600 |
| Activity | 0.0 | 7.0 | 8.3 | 8.3 | 6.4 | 3.9 | 2.5 | 0.4 |

These results indicate that the activity of the nickel metal formed declines for reduction temperatures above 300° C. and below 250° C. Because reduction is faster at 300° C., and maximal activity is achieved, it is the preferred reduction temperature for nickel oxide prepared at 300° C. using the equipment employed.

Examples 17 to 21

This series of experiments is designed to illustrate an optimal calcination temperature for BNC. Samples of BNC are calcined in air in a muffle furnace at the temperatures shown below. The calcination at 200° C. is conducted for 16 hours. At all other temperatures, the samples are calcined for 1 hour. The sample calcined at 200° C. has residual BNC in the nickel oxide, while the remaining samples have no detectable BNC residue. After calcination, all of the nickel oxide samples are reduced for 2 hours in hydrogen flowing at 300° C. the activities of the samples are as follows.

|  | Example | | | | |
| --- | --- | --- | --- | --- | --- |
|  | 17 | 18 | 19 | 20 | 21 |
| Temperature (° C.) | 200 | 300 | 400 | 500 | 600 |
| Activity | 7.1 | 8.3 | 7.9 | 10.1 | 13.0 |

These results indicate that elevated calcination temperatures give increased nickel activity levels.

In the following examples, the nickel metal powders are handled by means known to the skilled person to avoid contact with air. A general test procedure consists of providing a reactor bottle equipped with a magnetic stir bar, into which reactants are charged while enclosed in glove box operating with a dry nitrogen atmosphere. To this bottle is added 80 gram of a 10% by weight Ligand A solution in a 3-pentenenitrile (3PN) solvent, 3.2 gram nickel metal powder, and 1.0 gram of anhydrous $ZnCl_2$. The reaction mixture within the reaction bottle is heated to 60° C. Filtered liquid samples from the reaction mixture are removed from the reactor bottle at intervals of one hour, with a final sample being taken after 24 hours. In those instances where no soluble nickel is detected, it is judged that the reaction produces less than about 20-50 ppm soluble nickel in the form of soluble nickel complexes of Ligand A.

Example 22 (Comparative)

In a comparative example, eight (8) pounds of basic nickel carbonate (BNC) is charged to a 6" diameter fluid bed reactor. The reactor is closed, air flow established at a velocity of 45 feet/min, and the reactor is heated at a rate of 15° C./min until the bed temperature reached 400° C. These calcining conditions are held for a period of 1 hour converting the BNC with evolution of carbon dioxide and water to nickel oxide. The reactor is then swept with nitrogen to remove substantially all of the oxygen. Hydrogen gas is introduced to the reactor at such a rate that the gas composition becomes 20% hydrogen and 80% nitrogen. The so-formed nickel oxide is reduced under these conditions for a period of 2 hours. The hydrogen flow is then stopped, and the reactor is purged with nitrogen. An attempt is made to remove the nickel product from the reactor via an eductor tube. It failed to remove the nickel metal. The reactor is then cooled to room temperature and the reactor opened. The nickel metal product consisted of an agglomerated non-flowable mass, not useful for further testing with Ligand A or for generating a nickel-ligand catalyst complex.

Example 23

Example 22 is repeated in the same manner but with the addition of water vapor as steam to the reducing gas to give a composition of 20% hydrogen, 20% steam, and 60% nitrogen, by volume. The nickel metal product is readily removed from the reactor, using the eductor tube, as a freely flowing powder. This Ni metal powder is reactive in the formation of the desired organo-phosphorus nickel catalyst, so that a soluble nickel-ligand complex is formed.

Example 24

Basic nickel carbonate (BNC) is fed to a tubular reactor containing a rotating auger to push the composition through the reactor. The reactor is heated with external electrical resistance strip heaters to a temperature of between 300° C. and 400° C. The basic nickel carbonate and the pure hydrogen are fed to the front of the reactor and moved through the reactor in a co-current flow regime. Reaction of the basic nickel carbonate with the hydrogen occurred along the length of the reactor forming nickel metal powder and the evolution of steam and carbon dioxide into the gas phase. The nickel metal product so-formed is freely flowing and is reactive for forming the nickel catalyst complex.

While not wishing to be held to a theory of operation, it is believed that the foregoing examples illustrate a beneficial effect of water vapor, in the form of steam, on these thermally induced processes. In particular, during the reduction step with hydrogen a freely flowing nickel powder is provided especially when steam is present, where the nickel powder is useful for preparing homogeneous organo-phosphorus nickel catalysts.

Example 26

A Procedyne 14-inch diameter fluidized bed reactor is used to evaluate the fluidization characteristics of various basic nickel carbonate (BNC) samples from different sources. As indicated in Table 2, BNC from three different commercial sources exhibit different tap densities and fluidization characteristics.

TABLE 2

| Property | BNC-2 | BNC-6 | BNC-8 |
| --- | --- | --- | --- |
| Min. Fluidization Velocity (ft/min) | 85 | 74 | 24 |
| Bed Expansion @ min fluidization | 53% | 58% | 114% |
| Tap Density (lb/ft$^3$) | 33 | 42.3 | 27.4 |
| Charge Capacity for 40 × 48 in reactor (lbs) | 857 | 1062 | 509 |
| Product per Batch (lbs) | 360 | 446 | 214 |

Conditions for optimal fluidization of BNC from different sources can therefore vary because fluidization characteristics are dependent on particle properties such as particle size distribution, particle density, shape of particles, etc. Differences in fluidization characteristics for BNC from different sources have an effect on batch productivity as indicated in Table 2. Use of a BNC material with consistent fluidization properties may avoid batch-to-batch adjustment of fluidization conditions, and avoid waste when fluidization conditions are not properly adjusted to accommodate different batch characteristics.

Example 27

To further evaluate different sources of BNC, the time for maximum conversion of BNC during calcination is measured at different temperatures (300-350-400° C.). The percent BNC conversion is monitored by observing the percent of total $CO_2$ gas released. FIG. 2 shows that the degree of BNC calcination decreases as the temperature decreases for a given fixed time. In general, at least BNC calcination is optimal for 1 hour or more. However, FIG. 2 shows that the calcination rate is not identical for different BNC sources.

Example 28

Different sources of BNC are tested to evaluate whether reduction occurs in these different BNC sources under the same conditions. Reduction of BNC is observed by monitoring hydrogen gas consumption by the BNC samples as a function of temperature.

Figure 3:
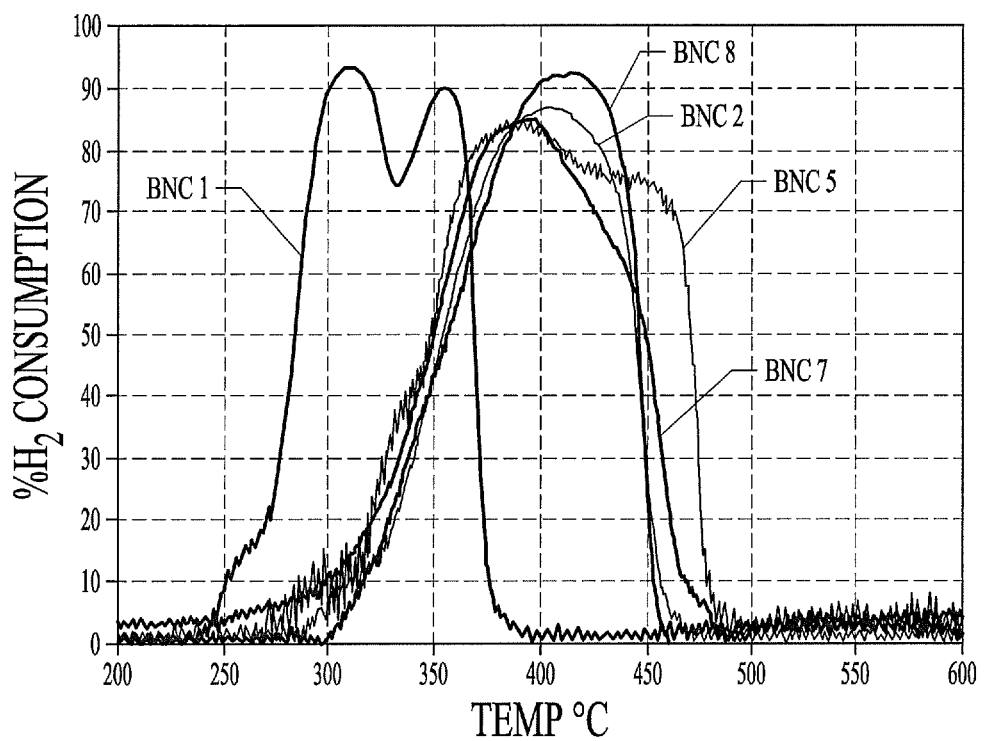
FIG. 3 graphically illustrates the percent consumption of hydrogen by BNC samples obtained from different commercial sources as a function of temperature.

As shown in FIG. 3, the temperature varies at which hydrogen is maximally consumed by the different BNC materials. The pattern of hydrogen uptake by calcined BNC samples #2, 5, 7, and 8 exhibit a single broadened hydrogen absorption maximum at around 400-450° C. This pattern is distinct from the pattern of hydrogen absorption exhibited for calcined BNC samples #3, 4, and 6 in FIG. 3, where two peaks of absorption are observed. Thus, there is a correlation between the response of BNC to processing conditions and the activity of particulate form of Ni produced.

The outlier, BNC sample #1, is a minimally active sample. As shown in FIG. 3, a double maximum of hydrogen absorption is observed when BNC sample #1 is reduced, and such reduction occurs at a somewhat lower temperature than the temperature maxima observed for BNC samples #2, 5, 7, and 8.

Example 29

The sources of BNC evaluated in Example 28 are tested for nickel metal reactivity after calcination and reduction. Nickel metal reactivity is assessed after calcination and reduction of BNC sample numbers 2-8 using procedures described herein. However, a sample of BNC, listed as BNC #1 in Table 2 above that is supplied by MetChem (an American distributor of BNC), is reduced without calcination. Fifty grams of BNC#1 material is reduced in hydrogen at a flow rate of 0.5 liter $H_2$/min at 400° C. for four hours. The reduction is done in a temperature controlled tube furnace. The reduction tube is taken into a dry box and the contents transferred to a bottle. The resulting powder is magnetic, indicating that nickel metal is produced by the reduction.

BNC samples #2-8 are processed in a similar manner, except that calcination pretreatment is also employed.

Each of the nickel samples from BNC samples #1-8 is evaluated for zero-valent nickel phosphorus ligand preparation. Under a nitrogen atmosphere, a reactor bottle is charged with 80 gm of a 5% by weight Ligand A solution in 3PN solvent, 3.2 gm of a selected calcined and reduced BNC (e.g., a nickel metal (Ni(0))-containing sample), and 0.5 gm of anhydrous $ZnCl_2$. After the reaction mixture inside the reactor bottle is heated to 60-80° C., filtered liquid samples are withdrawn and analyzed. The presence of high levels of soluble nickel indicates the nickel metal-containing sample is reactive. Table 3 shows which BNC samples yield active nickel preparations after reduction.

TABLE 3

| Nickel Sample Activity | |
| --- | --- |
| BNC No | Active Ni |
| 1 | Yes |
| 2 | Yes |
| 3 | No |
| 4 | No |
| 5 | Yes |

TABLE 3-continued

| Nickel Sample Activity | |
| --- | --- |
| BNC No | Active Ni |
| 6 | No |
| 7 | Yes |
| 8 | Yes |

In Table 3, "Active Ni" means that the Ni metal prepared by reduction from the corresponding BNC forms ligand complexes better than BNC sample #1, the Ni powder obtained from the MetChem BNC via a one-step reduction process (i.e., not including calcination pretreatment). Sample 1 has nickel activity barely sufficient to enable the efficient preparation of the zero-valent nickel phosphorus ligand complexes suitable for use as a hydrocyanation catalyst. Thus, BNC sample #3, #4 and #6 provide poorly reactive nickel metal under calcination/reduction conditions where BNC sample #2, #5, #7 and #8 provide active nickel metal preparations.

Figure 4:
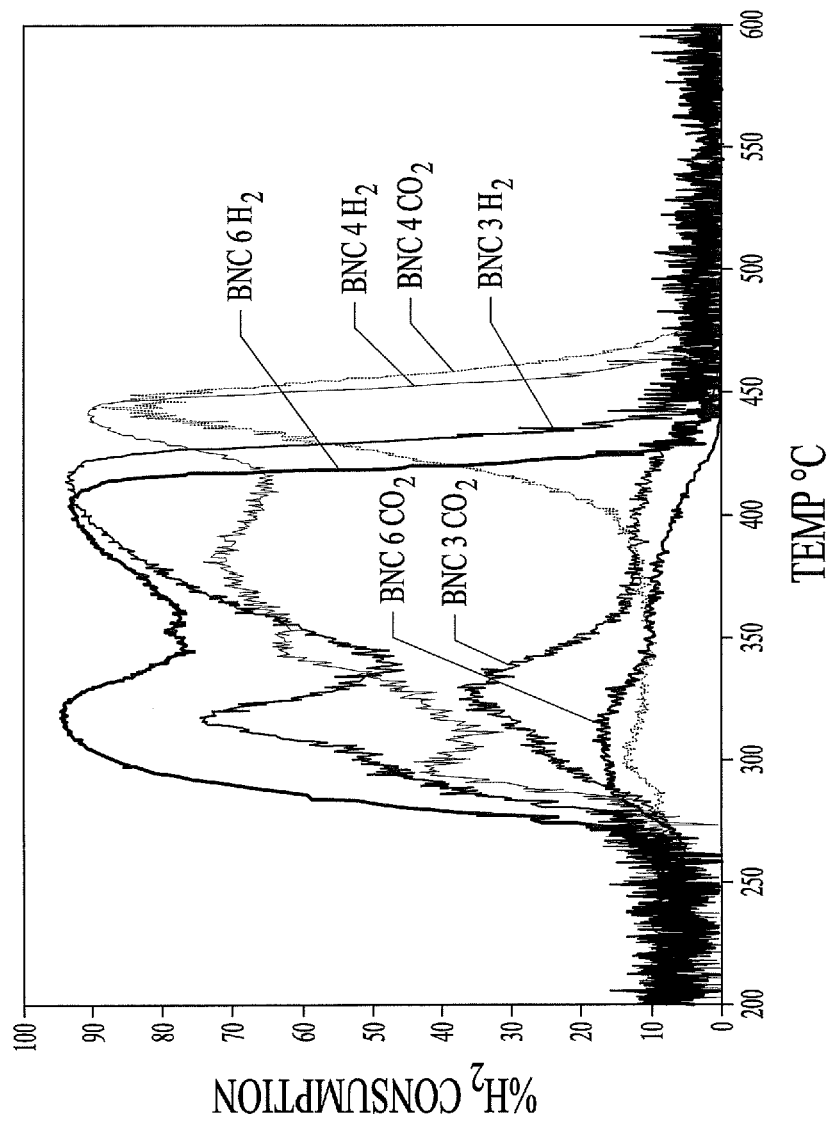
FIG. 4 graphically illustrates the percent consumption of hydrogen by different nickel oxide samples that are obtained after calcination of BNC samples from different commercial sources as a function of temperature, where the evolution of carbon dioxide is simultaneously measured. Nickel generated from these BNC #3, #4 and #6 sources is poorly reactive.

To evaluate this further, the BNC samples that provide poorly reactive nickel preparations are calcined to generate nickel oxide-containing samples. The consumption of hydrogen during reduction of these nickel oxide-containing samples is then observed as a function of temperature while simultaneously observing whether carbon dioxide is also released. As shown in FIG. 4, BNC sources that give rise to poorly reactive nickel metal release significant carbon dioxide during reduction with hydrogen, indicating that the calcination of these BNC samples may not be complete.

Example 30 (Comparative)

Figure 5:
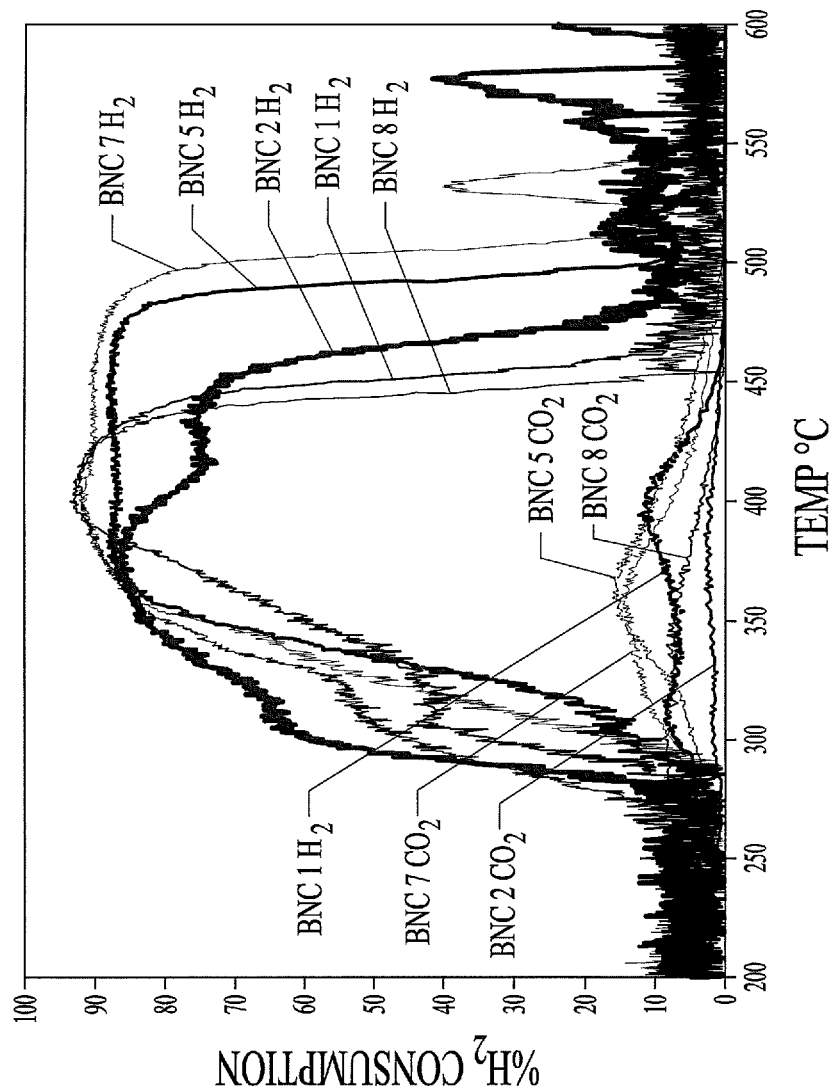
FIG. 5 graphically illustrates the percent consumption of hydrogen by different nickel oxide samples obtained after calcination of BNC samples from different commercial sources as a function of temperature, where the evolution of carbon dioxide is simultaneously measured. The reactivity of nickel generated from these BNC #1, #2, #5, #7 and #8 sources is acceptable, although the reactivity of nickel generated from BNC #1 is typically quite low.

Example 29 is repeated using other sources of BNC that provide nickel metal with acceptable reactivity after calcination and reduction. As shown in FIG. 5, NiO produced by these acceptably reactive BNC samples generally release less carbon dioxide during reduction to nickel metal.

Statements Describing Aspects of the Invention

Various statements of the present invention are described below as exemplary features:

Statement 1 provides a method for the production of nickel metal (Ni(0)) from a nickel(II)-containing composition comprising steps of:
(a) providing a nickel(II)-containing composition and a gas to a fluidizing bed reactor, wherein the gas is flowing and substantially supporting solids from the composition; and
(b) reducing nickel in the nickel(II)-containing composition to thereby produce nickel metal (Ni(0)) from the nickel(II)-containing composition;

wherein the composition comprises nickel(II)-containing substances selected from a group consisting of: basic nickel carbonate, nickel carbonate, nickel bicarbonate, nickel oxalate, nickel formate, nickel squarate, nickel oxide and nickel hydroxide.

Statement 2 provides a method for the production of nickel metal (Ni(0)) from a nickel(II)-containing composition comprising steps of:
(a) providing a nickel(II)-containing composition and a gas to a fluidizing bed reactor, wherein the gas comprises steam, and wherein the gas is flowing and substantially supporting solids from the composition; and
(b) reducing nickel in the nickel(II)-containing composition to thereby produce nickel metal (Ni(0)) from the nickel(II)-containing composition.

Statement 3 provides the method of any of Statements 1-2 for the production of nickel metal (Ni(0)) from a nickel(II)-containing composition, further comprising calcining the nickel(II)-containing composition prior to reducing the nickel.

Statement 4 provides the method of method of any of Statements 1-3 for the production of nickel metal (Ni(0)) from a nickel(II)-containing composition, further comprising calcining the nickel(II)-containing composition, wherein the calcining is performed under calcining conditions.

Statement 5 provides the method of any of Statements 1-4 for the production of nickel metal (Ni(0)) from a nickel(II)-containing composition, further comprising calcining the nickel(II)-containing composition under calcining conditions comprising providing a gas to the fluidizing bed reactor that includes oxygen.

Statement 6 provides the method of any of Statements 1-5 for the production of nickel metal (Ni(0)) from a nickel(II)-containing composition, further comprising calcining the nickel(II)-containing composition under calcining conditions comprising providing a gas to the fluidizing bed reactor that comprises air.

Statement 7 provides the method of any of Statements 1-6, further comprising calcining the nickel(II)-containing composition under calcining conditions that comprise operating the fluidized bed for a time and at a temperature sufficient for generating nickel oxide within the nickel(II)-containing composition.

Statement 8 provides the method of any of Statements 1-7 for the production of nickel metal (Ni(0)) from a nickel(II)-containing composition, further comprising calcining the nickel(II)-containing composition at a temperature of about 250° C. to about 600° C.

Statement 9 provides the method of any of any of Statements 1-8 for the production of nickel metal (Ni(0)) from a nickel(II)-containing composition, further comprising calcining the nickel(II)-containing composition for a time of about 10 minutes to 6 hours.

Statement 10 provides the method of any of any of Statements 1-9 for the production of nickel metal (Ni(0)) from a nickel(II)-containing composition, further comprising calcining the nickel(II)-containing composition to yield a calcined product with a carbon:nickel atomic ratio of less than one.

Statement 11 provides the method of any of Statements 1-10 for the production of nickel metal (Ni(0)) from a nickel(II)-containing composition, wherein reducing nickel comprises adapting conditions in the fluidizing bed to comprise reducing conditions.

Statement 12 provides the method of any of Statements 1-11 for the production of nickel metal (Ni(0)) from a nickel(II)-containing composition, wherein reducing nickel comprises adapting conditions in the fluidizing bed to comprise reducing conditions that comprise operating the fluidizing bed reactor for a time and at a temperature sufficient for reducing nickel(II) in the nickel(II)-containing composition to nickel(0) metal.

Statement 13 provides the method of any of Statements 1-12 for the production of nickel metal (Ni(0)) from a nickel (II)-containing composition, wherein reducing nickel comprises adapting conditions in the fluidizing bed to comprise reducing conditions that comprise introducing a reductant into the gas.

Statement 14 provides the method of any of Statements 1-13 for the production of nickel metal (Ni(0)) from a nickel (II)-containing composition, wherein reducing nickel comprises adapting conditions in the fluidizing bed to comprise reducing conditions that comprise introducing a reductant gas that comprises hydrogen.

Statement 15 provides the method of any of Statements 1-14 for the production of nickel metal (Ni(0)) from a nickel (II)-containing composition, wherein reducing nickel comprises adapting conditions in the fluidizing bed to a temperature of about 250° C. to about 450° C.

Statement 16 provides the method of any of Statements 1-15 for the production of nickel metal (Ni(0)) from a nickel (II)-containing composition, wherein reducing nickel comprises adapting conditions in the fluidizing bed to a temperature of about 250° C. to about 350° C.

Statement 17 provides the method of any of Statements 1-16 for the production of nickel metal (Ni(0)) from a nickel (II)-containing composition, wherein reducing nickel comprises adapting conditions in the fluidizing bed to comprise reducing conditions for a time of about 10 minutes to about 4 hours.

Statement 18 provides the method of any of Statements 1-17 wherein, the nickel(II)-containing composition comprises basic nickel carbonate that is prepared by contacting nickel(II) ions dissolved in water with carbonate ions, bicarbonate ions, or a combination of carbonate ions and bicarbonate ions.

Statement 19 provides the method of any of Statements 1-18 for the production of nickel metal (Ni(0)) from a nickel (II)-containing composition, wherein 1-20 batches of the nickel-containing composition are processed to produce nickel metal (Ni(0)).

Statement 20 provides the method of any of Statements 1-19 for the production of nickel metal (Ni(0)) from a nickel (II)-containing composition, wherein the fluidizing bed reactor is maintained at a temperature of about 200° C. to about 600° C. for at least about 10 hours.

Statement 21 provides the method of any of Statements 1-20 for the production of nickel metal (Ni(0)) from a nickel (II)-containing composition, wherein the gas comprises steam sufficient to generate a free-flowing Ni(0) metal powder.

Statement 22 provides the method of any of Statements 1-21 for the production of nickel metal (Ni(0)) from a nickel (II)-containing composition, wherein the gas comprises steam generated in situ.

Statement 23 provides the method of any of Statements 1-22 for the production of nickel metal (Ni(0)) from a nickel (II)-containing composition, wherein the gas comprises about 0.1% to about 50 volume percent steam.

Statement 24 provides the method of any of Statements 1-23 for the production of nickel metal (Ni(0)) from a nickel (II)-containing composition, wherein the gas comprises about 0.1% to 20% volume percent steam that is externally added to the gas.

Statement 25 provides the method of any of Statements 1-24 for the production of nickel metal (Ni(0)) from a nickel (II)-containing composition, wherein the gas comprises about 5% to about 20% steam that is externally added to the gas.

Statement 26 provides a nickel metal (Ni(0) preparation made by the method of any of Statements 1-25.

Statement 27 provides a method for making a complex of nickel metal (Ni(0)) and one or more phosphorus-containing ligands comprising: contacting the one or more phosphorus containing ligands with nickel metal (Ni(0)) made by the method of any of Statements 1-25.

Statement 28 provides a method for making a complex of nickel metal (Ni(0)) and one or more phosphorus-containing ligands comprising: contacting the one or more phosphorus containing ligands with nickel metal (Ni(0)) in a solvent, wherein the nickel metal (Ni(0) is produced from nickel(II)-containing composition in a fluidizing bed reactor.

Statement 29 provides the method of Statement 28 for making a complex, wherein at least a portion of the nickel metal (Ni(0)) in the nickel complex is produced by a method comprising:

providing a nickel(II)-containing composition and a gas to a fluidizing bed reactor, wherein the gas is flowing and substantially supporting solids in the composition; and reducing nickel in the nickel(II)-containing composition to thereby produce nickel metal (Ni(0)) from the nickel-containing composition.

Statement 30 provides the method of any of Statements 28 or 29 for making a complex, wherein the fluidizing bed reactor comprises a gas containing steam.

Statement 31 provides the method of any of Statements 28-30 for making a complex, wherein the fluidizing bed reactor comprises a gas comprising about 0.1% to about 50 volume percent steam.

Statement 32 provides the method of any of Statements 28-31 for making a complex, wherein the fluidizing bed reactor comprises a gas comprising about 0.2% to 20% volume percent steam.

Statement 33 provides the method of any of Statements 28-32 for making a complex, wherein the fluidizing bed reactor comprises a gas comprising about 5% to about 20% steam.

Statement 34 provides the method of any of Statements 28-33 for making a nickel complex, wherein at least a portion of the nickel metal (Ni(0)) in the nickel complex is produced from a first nickel(II)-containing composition comprising nickel(II), and the first nickel(II)-containing composition is converted to the nickel metal (Ni(0)) in two stages, comprising a calcination stage followed by a reduction stage;

wherein, the calcination stage comprises heating the first nickel(II)-containing composition and thereby generating a second nickel(II)-containing composition comprising nickel (II), and the reduction stage comprises reducing the second nickel (II)-containing composition to produce the nickel metal (Ni(0)).

Statement 35 provides the method of Statement 34, wherein the first nickel(II)-containing composition comprises: a nickel(II)-containing composition comprising basic nickel carbonate, nickel carbonate, nickel bicarbonate, nickel oxalate, nickel formate, nickel squarate, nickel hydroxide, nickel oxide and combinations thereof.

Statement 36 provides the method of any of Statements 34 or 35, wherein the first nickel(II)-containing composition is prepared by contacting nickel(II) ions dissolved in water with carbonate ions, bicarbonate ions, or a combination of carbonate ions and bicarbonate ions.

Statement 37 provides the method of any of Statements 34-36, wherein the second nickel(II)-containing composition comprises nickel(II) hydroxide, nickel(II) oxide and combinations thereof.

Statement 38 provides the method of any of Statements 34-37, wherein the heating the first nickel(II)-containing composition yields a second nickel composition with a carbon:nickel atomic ratio of less than one.

Statement 39 provides a method of identifying whether a basic nickel carbonate test sample will yield a nickel particulate form with nickel atoms that reach an equilibrium of complex formation with one or more phosphorus-containing ligands within two hours, where the method comprises:

(a) calcining a basic nickel carbonate test sample; and
(b) observing whether the test sample gives off more or less carbon dioxide compared to a control basic nickel carbonate sample;

wherein upon reduction the basic nickel carbonate test sample will yield an active nickel particulate form with nickel atoms that reach an equilibrium of complex formation with one or more phosphorus-containing ligands within about 2 hours when the basic nickel carbonate test sample gives off less carbon dioxide than the control basic nickel carbonate; and wherein upon reduction the control basic nickel will yield a nickel particulate form with nickel atoms that does not reach an equilibrium of complex formation with one or more phosphorus-containing ligands within about 2 hours.

Statement 40 provides a method of identifying whether a basic nickel carbonate test sample will yield a nickel particulate form with nickel atoms that reach an equilibrium of complex formation with one or more phosphorus-containing ligands within two hours, where the method comprises:

(a) calcining a basic nickel carbonate test sample to produce a calcination product;
(b) reducing nickel(II) in the calcination product to nickel metal (Ni(0)); and
(c) observing whether the calcination product gives off carbon dioxide during reduction;

wherein the basic nickel carbonate test sample will yield an active nickel particulate form with nickel atoms that reach an equilibrium of complex formation with one or more phosphorus-containing ligands within about 2 hours when the calcination product derived from the basic nickel carbonate test sample gives off less carbon dioxide than a control calcination product during reduction; and wherein the control calcination product will yield a nickel particulate form with nickel atoms that do not reach an equilibrium of complex formation with one or more phosphorus-containing ligands within about 2 hours.

Statement 41 provides a method of identifying whether a nickel test sample will yield a nickel particulate form with nickel atoms that reach an equilibrium of complex formation with one or more phosphorus-containing ligands within two hours, where the method comprises:

(a) reducing the nickel test sample with hydrogen; and
(b) observing whether the nickel test sample exhibits a single peak of hydrogen absorption between about 350° C. and 450° C. during reduction;

wherein the nickel test sample will yield an active nickel particulate form with nickel atoms that reach an equilibrium of complex formation with one or more phosphorus-containing ligands within two hours when the nickel test sample exhibits a single peak of hydrogen absorption between about 350° C. and 450° C. during reduction.

Statement 42 provides the method of statement 41, wherein the nickel test sample is basic nickel carbonate, nickel oxide, nickel hydroxide, or a mixture thereof.

Statement 43 provides the method of any of statements 39-42, wherein the basic nickel carbonate test sample or the nickel test sample yields an active nickel particulate form with nickel atoms that reach an equilibrium of complex formation with one or more phosphorus-containing ligands within one hour.

Statement 44 provides the method of any of statements 39-43, wherein the basic nickel carbonate test sample or the nickel test sample yields an active nickel particulate form with nickel atoms that reach an equilibrium of complex formation with one or more phosphorus-containing ligands within 30 minutes.

Statement 45 provides the method of any of statements 39-44, further comprising forming a complex between the nickel atoms of an active nickel particulate form and one or more phosphorus-containing ligands to generate a hydrocyanation catalyst.

Statement 46 provides a method of avoiding waste, comprising:
(a) calcining a basic nickel carbonate test sample;
(b) observing whether the test sample gives off more or less carbon dioxide compared to a control basic nickel carbonate sample during calcination; and
(c) optionally preparing a nickel-ligand complex from nickel atoms derived from the source of the basic nickel carbonate test sample if the test sample gives off less carbon dioxide compared to the control basic nickel carbonate sample during calcination;

wherein after reduction the basic nickel carbonate test sample will not yield an active nickel particulate form with nickel atoms that reach an equilibrium of complex formation with one or more phosphorus-containing ligands within about 2 hours when the basic nickel carbonate test sample gives off more carbon dioxide than the control basic nickel carbonate during calcination; and wherein after reduction the control basic nickel carbonate yields a nickel preparation with nickel atoms that does not reach an equilibrium of complex formation with one or more phosphorus-containing ligands within about 2 hours after mixing in a organonitrile solvent.

Statement 47 provides the method of statement 46, wherein waste is avoided by identifying a basic nickel carbonate test sample that gives off more carbon dioxide than the control basic nickel carbonate during calcination, and not using the basic nickel carbonate source from which the basic nickel carbonate test sample was obtained to make a nickel particulate form for use in a hydrocyanation catalyst.

Statement 48 provides a method of avoiding waste, comprising:
(a) reducing the nickel test sample with hydrogen; and
(b) observing whether the nickel test sample exhibits a single peak of hydrogen absorption between about 350° C. and 450° C. during reduction; and
(c) optionally preparing a nickel-ligand complex from nickel atoms derived from the source of the nickel test sample if the test sample exhibits a single peak of hydrogen absorption between about 350° C. and 450° C. during reduction.

Statement 49 provides the method of statement 48, wherein waste is avoided by observing whether the nickel test sample exhibits a single peak of hydrogen absorption between about 350° C. and 450° C. during reduction and not using the source from which the test nickel sample was obtained to make a nickel particulate form for use in a hydrocyanation catalyst if the nickel test sample does not exhibit a single peak of hydrogen absorption between about 350° C. and 450° C. during reduction.

Statement 50 provides a method of avoiding waste, comprising:
(a) calcining a basic nickel carbonate test sample to provide a test calcination product;
(b) reducing nickel(II) in the test calcination product to nickel metal (Ni(0)); and
(c) observing whether the test calcination product gives off more or less carbon dioxide during reduction compared to a control calcination product;
(d) optionally preparing a nickel-ligand complex from nickel atoms derived from the source of the basic nickel carbonate test sample if the test calcination product gives off less carbon dioxide during reduction compared to the control calcination product during reduction;

wherein the basic nickel carbonate test sample will not yield an active nickel particulate form with nickel atoms that reach an equilibrium of complex formation with one or more phosphorus-containing ligands within about 2 hours when the test calcination product gives off more carbon dioxide than the control calcination product during reduction.

Statement 51 provides the method of statement 50, wherein waste is avoided by identifying a test calcination product that gives off more carbon dioxide than the control calcination product, and not using the basic nickel carbonate source from which the test calcination product was obtained to make a nickel particulate form for use in a hydrocyanation catalyst.

Statement 52 provides the method of any of statements 39-51, wherein the one or more phosphorus-containing ligands is Ligand A

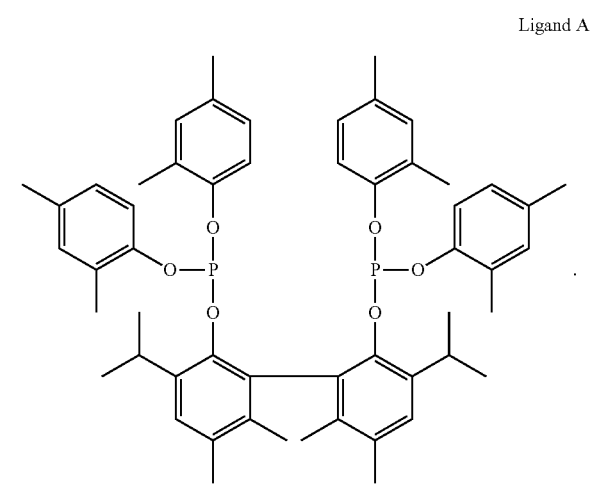

Ligand A

Statement 53 provides the method of any of statements 39-52, wherein an equilibrium of complex formation is reached within about 2 hours when about 4 wt % nickel obtained from the basic nickel carbonate or the nickel test sample is mixed at about 60° C. to 80° C. in an organonitrile solvent with about 0.5 to 2.5 moles Lewis acid per mole bidentate phosphorus-containing ligand.

Statement 54 provides the method of any of statements 39-53, wherein an equilibrium of complex formation is reached within about 1 hour when about 4 wt % nickel obtained from the basic nickel carbonate or the nickel test sample is mixed at about 60° C. to 80° C. in an organonitrile solvent with about 0.5 to 2.5 moles Lewis acid per mole bidentate phosphorus-containing ligand.

Statement 55 provides the method of any of statements 39-54, wherein an equilibrium of complex formation is reached within about 30 minutes when about 4 wt % nickel obtained from the basic nickel carbonate or the nickel test sample is mixed at about 60° C. to 80° C. in an organonitrile solvent with about 0.5 to 2.5 moles Lewis acid per mole bidentate phosphorus-containing ligand.

Statement 56 provides the composition or method of any or any combination of Statements 1-55 is optionally configured such that all elements or options recited are available to use or select from.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific compositions and methods described herein are representative, exemplary and not intended as limitations on the scope of the invention. Other objects, aspects, and features will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by aspects and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "a catalyst" or "a ligand" includes a plurality of such compounds, catalysts or ligands, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or features or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed:

1. A method for the production of nickel metal (Ni(0)) comprising:
   calcining a first nickel(II)-containing composition to generate a second nickel(II)-containing composition;
   providing the second nickel(II)-containing composition and a gas to a fluidizing bed reactor, wherein the gas is flowing and substantially supporting solids from the composition;
   wherein the gas comprises a reductant and steam; and
   reducing nickel in the second nickel(II)-containing composition at about 250° C. to about 450° C. to thereby produce nickel metal (Ni(0)) from the second nickel(II)-containing composition;
   wherein the first nickel(II)-containing composition comprises nickel(II)-containing substances selected from a group consisting of: basic nickel carbonate, nickel carbonate, nickel bicarbonate, nickel oxalate, nickel formate, nickel squarate, nickel oxide and nickel hydroxide.

2. The method of claim 1, further comprising calcining the first nickel(II)-containing composition under calcining conditions.

3. The method of claim 1, further comprising calcining the first nickel(II)-containing composition by a method comprising providing a gas to the fluidizing bed reactor that comprises oxygen.

4. The method of claim 1, further comprising calcining the first nickel(II)-containing composition by a method comprising operating the fluidized bed for a time and at a temperature sufficient for generating nickel oxide within the nickel(II)-containing composition.

5. The method of claim 1, further comprising calcining the first nickel(II)-containing composition using calcining conditions that yield a calcined product with a carbon:nickel atomic ratio of less than one.

6. The method of claim 1, further comprising calcining the first nickel(II)-containing composition at a temperature of about 250° C. to about 600° C.

7. The method of claim 1, further comprising calcining the first nickel(II)-containing composition for a time of about 10 minutes to 6 hours.

8. The method of claim 1, wherein the reductant comprises hydrogen.

9. The method of claim 1, wherein reducing nickel comprises operating the fluidizing bed reactor for a time and at a temperature sufficient for reducing nickel(II) in the second nickel(II)-containing composition to nickel(0) metal.

10. The method of claim 1, wherein reducing nickel comprises operating the fluidizing bed reactor at a temperature of about 250° C. to about 350° C.

11. The method of claim 1, wherein reducing nickel comprises operating the fluidizing bed reactor for about 10 minutes to about 4 hours.

12. The method of claim 1, wherein the gas comprises steam generated in situ.

13. The method of claim 1, wherein the gas comprises added steam charged into the reactor from an external source.

14. The method of claim 1, wherein the gas comprises sufficient steam to produce free-flowing nickel metal (Ni(0)).

15. The method of claim 1, wherein the gas comprises about 1 to about 50 volume percent steam.

16. The method of claim 1, wherein the gas comprises hydrogen as reductant and about 1 to about 20 volume percent added steam charged into the reactor from an external source.

17. The method of claim 1, wherein the first nickel(II)-containing composition comprises basic nickel carbonate that is prepared by contacting nickel(II) ions dissolved in water with carbonate ions, bicarbonate ions, or a combination of carbonate ions and bicarbonate ions.

18. The method of claim 1, wherein the fluidizing bed reactor is maintained at a temperature of about 250° C. to about 450° C. for at least about 10 hours.

19. The method of claim 1, for the production of nickel metal (Ni(0)) from a nickel(II)-containing composition, wherein 1-20 batches of the nickel-containing composition are processed to produce nickel metal (Ni(0)).

20. The method of claim 1, wherein nickel metal (Ni(0)) is agglomerated when generated by reducing a second nickel (II)-containing composition in the gas at about 250° C. to about 450° C. when no steam is present in the gas.

21. The method of claim 1, wherein nickel metal (Ni(0)) is agglomerated when generated by reducing a second nickel (II)-containing composition in the gas at about 250° C. to about 450° C. when no steam is added to the gas.

22. A method for making a complex of nickel metal (Ni(0)) and a phosphorus-containing ligand comprising:
contacting the phosphorus-containing ligand with nickel metal (Ni(0)), wherein at least a portion of the nickel metal (Ni(0)) is produced by a method comprising:
calcining a first nickel(II)-containing composition to generate a second nickel-containing composition;
providing the second nickel(II)-containing composition and a gas to a fluidizing bed reactor, wherein the gas is flowing and substantially supporting solids in the second nickel(II)-containing composition; and
reducing nickel in the second nickel(II)-containing composition at about 250° C. to about 450° C. to thereby produce nickel metal (Ni(0)) from the second nickel-containing composition;
wherein the gas in the fluidizing bed reactor comprises a reductant and steam.

23. The method of claim 22, wherein the gas comprises steam generated in situ.

24. The method of claim 22, wherein the gas comprises added steam charged into the reactor from an external source.

25. The method of claim 22, wherein the gas comprises sufficient steam to produce free-flowing nickel metal (Ni(0)).

26. The method of claim 22, wherein the gas comprises about 0.1% to about 50 volume percent steam.

27. The method of claim 22, wherein the gas comprises hydrogen as reductant and about 1 to about 20 volume percent added steam charged into the reactor from an external source.

28. The method of claim 22 for making a nickel complex, wherein at least a portion of the nickel metal (Ni(0)) in the nickel complex is produced from a first nickel(II)-containing composition comprising nickel(II), and the first nickel(II)-containing composition is converted to the nickel metal (Ni (0)) in two stages, comprising
a calcination stage followed by a reduction stage;
wherein the calcination stage comprises heating the first nickel(II)-containing composition to thereby generate a second nickel(II)-containing composition comprising nickel(II), and
the reduction stage comprises reducing the second nickel (II)-containing composition to produce the nickel metal (Ni(0)).

29. The method of claim 28, wherein the first nickel(II)-containing composition comprises: a nickel(II)-containing composition comprising basic nickel carbonate, nickel carbonate, nickel bicarbonate, nickel oxalate, nickel formate, nickel squarate, nickel hydroxide, nickel oxide and combinations thereof.

30. The method of claim 28, wherein the first nickel(II)-containing composition is prepared by contacting nickel(II) ions dissolved in water with carbonate ions, bicarbonate ions, or a combination of carbonate ions and bicarbonate ions.

31. The method of claim 28, wherein the second nickel(II)-containing composition comprises nickel(II) hydroxide, nickel(II) oxide and combinations thereof.

32. The method of claim 28, wherein heating the first nickel(II)-containing composition yields a second nickel(II)-containing composition with a carbon:nickel atomic ratio of less than one.

33. The method of claim 28, wherein the calcination stage comprises heating the first nickel(II)-containing composition in the fluid bed reactor.

34. The method of claim 28, wherein the calcination stage comprises heating the first nickel(II)-containing composition in a fluid bed reactor in an atmosphere comprising steam.

35. The method of claim 1, wherein calcining the nickel (II)-containing composition prior to reducing the nickel comprises heating the nickel(II)-containing composition in a fluid bed reactor in an atmosphere comprising steam.

* * * * *